US008207132B2

(12) United States Patent
Ross et al.

(10) Patent No.: US 8,207,132 B2
(45) Date of Patent: Jun. 26, 2012

(54) RECOMBINANT VACCINES AGAINST CALIGID COPEPODS (SEA LICE) AND ANTIGEN SEQUENCES THEREOF

(75) Inventors: Neil W. Ross, Halifax (CA); Stewart C. Johnson, Shad Bay (CA); Mark D. Fast, Halifax (CA); Kathryn Vanya Ewart, Halifax (CA)

(73) Assignee: National Research Council of Canada, Ottawa, Ontario (CA)

( * ) Notice: Subject to any disclaimer, the term of this patent is extended or adjusted under 35 U.S.C. 154(b) by 69 days.

(21) Appl. No.: 11/572,719

(22) PCT Filed: Jul. 28, 2005

(86) PCT No.: PCT/CA2005/001178
§ 371 (c)(1),
(2), (4) Date: Jan. 26, 2007

(87) PCT Pub. No.: WO2006/010265
PCT Pub. Date: Feb. 2, 2006

(65) Prior Publication Data
US 2008/0003233 A1 Jan. 3, 2008

Related U.S. Application Data

(60) Provisional application No. 60/591,626, filed on Jul. 28, 2004.

(51) Int. Cl.
*A61K 38/08* (2006.01)
(52) U.S. Cl. .................................................. 514/21.7
(58) Field of Classification Search .................. 514/21.7
See application file for complete search history.

(56) References Cited

U.S. PATENT DOCUMENTS
6,248,329 B1 * 6/2001 Chandrashekar et al. . 424/191.1
2002/0013955 A1 * 1/2002 Ogden et al. .................... 800/20

FOREIGN PATENT DOCUMENTS
JP          7 163361 A        6/1995
WO      WO 88/03953 A1       6/1988
WO       20070039599 A1      4/2007

OTHER PUBLICATIONS

Ellis (Chapter 29 of Vaccines, Plotkin, et al. (eds) WB Saunders, Philadelphia, 1998, 2 pages cover sheet and p. 571, ).*
Bowie et al (Science, 1990, 247:1306-1310).*
Raynard S. et al., Development of a vaccine for the control of sea lice (*Lepeophtheirus salmonis* and *Caligus elongatus*) in Atlantic salmon (Saline salar)., ICES Council Meeting Papers, ICES-CM-1994/F: 17. Counc.Meet. of the Int. Counc. for the Exploration of the Sea. Sep. 22-30, 1994 St. John's Newfoundland (Canada), 6 pages.*
Johnson et al 2002 Parasitol Res vol. 88 pp. 789-796.*
Woo, "Immunization Against Parasitic Diseases of Fish", Developments in Biological Standardization, vol. 90, Jan. 1, 1997, pp. 233-241, XP000872281, ISSN: 0301-5149.

European Patent Application No. 05770065.0, Search Report dated Apr. 3, 2009.
Raynard et al., Development of vaccines against sea lice, Pest management Science, Jun. 2002, vol. 58, No. 6, pp. 569-575, ISSN 1526-498X, pp. 569-575.
Raynard et al., "Development of a vaccine for the control of sea lice (*Lepeophtheirus salmons* and *Caligus elongatus*) in Atlantic salmon (Salmo solar)", ICES Council Meeting Papers, ICES-CM-1994/F:17, Counc. Meet. of the Int. Counc. for the Exploraton of the Sea, Sep. 22-23, 1994, pp. 1-6.
Labus et al., "Identification and expression of antigens from *Lepeophtheirus salmonis* for the use in vaccination trials", Biochemical Society Transactions, May 1996, vol. 24, No. 2, p. 254S.
Grayson et al., "Immunization of Atlantic salmon against the salmon louse: Identification of antigens and effects on louse fecundity", Journal of Fish Biology, Dec. 1995, vol. 47, Supp. A. pp. 85-94.
Kvamme et al., "The cloning and characertization of full-length trypsins from the salmon louse *Lepeophtheirus salmonis*", Mol. Biocehm. Parasitol, Aug. 2004, vol. 136, No. 2, pp. 303-307.
Kvamme et al., "Molecular characterization of five trypsin-like peptidase transcripts from salmon louse (*Lepeophtheirus salmonis*) intestine", International Journal for Parasitology, Jun. 2004, vol. 34, No. 7, pp. 823-832.
Jenkins et al, "The extraction and analysis of potential candidate vaccine antigens from the salmon louse *Lepeophtheirus salmonis* (Kroyer 1837)", Ellis Horwood Series in Aquaculture and Fisheries Support Pathogens of wild and farmed fish, Oct. 1993, pp. 311-322.
Roper et al., "The immunocytochemical localisation of potential candidate vaccine antigens from the salmon louse, *Lepeophtheirus salmonis* (Kroyer 1837)", Aquaculture, May 1995, vol. 132, pp. 221-232.
PCT Patent Application No. PCT/CA2005/001178, International Search Report dated Nov. 21, 2005.
European Patent Application No. 11171461.4, European Search Report dated Nov. 21, 2011.
European Patent Application No. 11171441.6, European Search Report dated Nov. 21, 2011.
European Patent Application No. 11171453.1, European Search Report dated Dec. 6, 2011.
European Patent Application No. 11171430.9, European Search Report dated Dec. 13, 2011.
European Patent Application No. 11171467.1, European Search Report dated Dec. 13, 2011.
European Patent Application No. 11171518.1, European Search Report dated Dec. 8, 2011.
Database Uniprot (Online), "Subname: Full=RE08669p; Subname: Fulll=Ribosomal protein L6, isoform B" XP002662672, retrieved from EBI accession No. Uniprot: Q9V9W3, 2 pages, May 1, 2000.
Database Uniprot (Online), "RecName: Full=Adhesive Plaque Matrix protein 2; AltName: Full=Foot protein 2; AltName: Full=MGFP-2; Short=MGFP2; Flags: Precursor" XP002662686, retrieved from EBI accession No. Uniprot: Q25464, 3 pages, Nov. 1, 1996.

(Continued)

*Primary Examiner* — Gary Nickol
*Assistant Examiner* — Nina Archie
(74) *Attorney, Agent, or Firm* — David A. Nauman; Borden Ladner Gervais LLP

(57) ABSTRACT

Molecular targets and vaccines against them in the treatment of sea lice infection of fish are provided, particularly caligid copepods. Vaccines targeted to *L. salmonis* trypsin are shown to reduce the quantity of sea lice present in challenged salmon from day 14 p.i. onward. Additional and novel molecular targets for vaccines are also provided.

9 Claims, 22 Drawing Sheets

OTHER PUBLICATIONS

Inoue, K., et al., "Mussel Adhesive Plaque Protein Genie is a Novel Member of Epidermal Growth Factor-like Gene Family", Journal of Biological Chemistry, The American Society of Biological Chemists, Inc., US, vol. 270, No. 12, pp. 6698-6701, Mar. 24, 1995.

Misra, Sima, et al., "Annotation of the Drosophila Melanogaster Euchromatic Genome: a Systematic Review", Genome Biology, Biomed Central Ltd., London, GB, vol. 3, No. 12, pp. 0083.1 to 0083.22, Dec. 31, 2002.

Database Uniprot (Online), "Subname: Full=Melanization-related protein" XP002663476, retrieved from EBI accession No. UNIPROT: Q9NDN7, 2 pages, Oct. 1, 2000.

Lee, Kwang Moon, et al., "Activated Phenoloxidase from Tenebrio Molitor Larvae Enhances the Synthesis of Melanin by Using a Vitellogenin-like protein in the Presence of Dopamine", European Journal of Biochemistry, Blackwell Publishing, Berlin, DE, vol. 267, No. 12, pp. 3695-3703, Jun. 1, 2000.

Fast, M D, et al., Enzymes released from *Lepeophtheirus salmonis* in Response to Mucus from different Salmonids, The Journal of Parasitology, American Society of Parasitologies, US, vol. 89, No. 1, pp. 7-13, Feb. 1, 2003.

Grayson, T H, et al., "Serum Responses to the Salmon Louse, *Lepeophtheirus salmonis* (Kroyer 1838), in Naturally Infected Salmonoids and Immunised Rainbow Trout, *Oncorhynchus mykiss* (Walbaum), and rabbits", Fish and Shellfish Immunology, Academic Press, London, GB, vol. 1, pp. 141-155, Apr. 1, 1991.

Fast, M D, et al., "*Lepeophtheirus salmonis* secretory/excretory products and their effects on Atlantic Salmon Immune Gene Regulation", Parasite Immunology, Blackwell Scientific Publications, Oxford, GB, vol. 29, No. 4, pp. 179-189, Apr. 1, 2007.

Database Uniprot (Online), "RecName: Full=Vitellogenin-1; Flags: Precursor", XP002663567, retrieved from EBI accession No. Uniprot: P55155, 1 page, Oct. 1, 1996.

Database Geneseq (Online), "Balanus amphitrite adhesion/metamorphosis-related protein Bcs-1", XP002663601, retrieved from EBI accession No. GSP: AAB23267, 1 page, Feb. 2, 2001.

* cited by examiner

FIG. 1 a)

Vitellogenin-like protein (SL-0903)

Nucleic acid sequence

GCAATACAAAATTATCCATGGATGTACTACCACAATTGACCATGTATATACTCTT
GACAATGTCACATATCCTTACACACCTACCTCATGCTGGACGTTGGCTTCTGGA
CACTGTTCCCCACATCCAACTTATGCAGTTTTTGTCAAAAAGTCTGCAGGATCTC
ATTTAGATGCTAAAATTTATTTGGGCGGTCACAGCATCGAATTCCAAACAAGTGG
CCCAAAGAAGATTAATGTTCTCATCAACGGTGAAGCTATTGATGTAGGAGAGGA
GGAACATGTTCATGAACAAGACGGACAAGAAATTTTCAAGGTCTTAAAATGGGG
ATCAAGTTACAGTGTTTACTCCTTCTTGAAAATCTGGGTAGTCTATGATGGCCAT
GCAGTCAGCTTAATCCCTGCTCCATCTGTTACGGGTCAACATTGCGGTTTGTGT
GGAAACTTCAACAGAAACCAATATGATGAATTTGAAAGCAAGGATGCTCATCAAT
TGAAGACATCCGACGAGCTTGTTGAAGATTATAAATGGAAGTGTTGAGAATTTAT
TTCTTTCATCGATTGATGGAGATATTTTTTACAATGATTCTATTATAT b)

Amino Acid sequence

QYKIIHGCTTTIDHVYTLDNVTYPYTPTSCWTLASGHCSPHP
TYAVFVKKSAGSHLDAKIYLGGHSIEFQTSGPKKINVLINGE
AIDVGEEEHVHEQDGQEIFKVLKWGSSYSVYSFLKIWVVYD
GHAVSLIPAPSVTGQHCGLCGNFNRNQYDEFESKDAHQLKT
SDELVEDYKWKC

FIG. 2 a)

SEP Protein 1 (SL-0547)

Nucleic acid sequence

GTCCGGTTCGGCAAATCTAAAATGTACCACAAGAAGGCAATCTATAAATTCTTGA
AGAAGACAACTCCCAAAAAGGTTGAGGCCAGTAAGCCCGCCTTCGTTGAGAAG
AAGGTCGGAGGTGCCAAGAATGGGGGTACTCGTATGGTTCGCGTCAAGAAGTT
GAAGAACGACTTCCCCACCATGGAAAGACGTGCTCATAGAATCGCCAAGAAGC
CTGAAAAGCTCTCTCGCAGGGTCCGTCCTACCCTCACCCCTGGAACTATTGCAG
TTATTCTTGCAGGTATCCACAAAGGAAAGAGAATCGTCATTCTCAAGGAGCTCTC
CAGTGGAATGCTTCTGATTTCTGGCCCCTTCAAGCTTAATAACTGCCCAATTAGA
AGGATTAATCAACGCTATTTGTTGGCCACATCAACCAAGCTCGATGTTTCATCCA
TTAAAATGCCCGAGAACATTAATGATGATTACTTCCGTCGTTTAAGAGCCGCCAA
GAAGCCAGCTGGTANTGTAT b)

Amino Acid sequence

V R F G K S K Met Y H K K A I Y K F L K K T T P K K V E A S K P A F V E K K V G G
A K N G G T R Met V R V K K L K N D F P T Met E R R A H R I A K K P E K L S R R V
R P T L T P G T I A V I L A G I H K G K R I V I L K E L S S G Met L L I S G P F K L N N
C P I R R I N Q R Y L L A T S T K L D V S S I K Met P E N I N D D Y F R R L R A A K
K P A G X V

FIG. 3 a)

SEP Protein 2 (SL-0858)

Nucleic acid sequence

AAGCCCTCTTTGATCTTCAGAAGGACCTCGATGGAGATGTGGATGTTGAACTCA
AGTTGGTCAAGAAAGGAATTGTCTCCATTCCCATCCCCTGCATTGAAAGCCCTT
CAGGCCTGCATTTGGGCTCTTGTTCCTACAAACTGGAGGAGATTGTCAGCAAAT
ATGCGTATTTCTTGTGTCCAGACTATTTTCCAGAGGGCCAAAGCTGTTCTTTCCC
TTTGAAGGCAGGACAATATGGAGGTGAGATCTCTGGTATTGTTCTACCTGACAT
CCCACCTTCCATTTCCAACCTCGCCAAGGGAACCATTCATGGAACTCTCTCTGT
GACCAGAAACGGGGAAGAAGTTTTCTGTATCAATGGAGATTTGAAAATGACAAA
TTAATCCTTGTTTCTGTATCCATATTTGAAGTCAATAAAATACTTCATTAATCT b)

Amino Acid sequence

-A L F D L Q K D L D G D V D V E L K L V K K G I V S I P I P C I E S P S G L H L G S
C S Y K L E E I V S K Y A Y F L C P D Y F P E G Q S C S F P L K A G Q Y G G E I S G I
V L P D I P P S I S N L A K G T I H G T L S V T R N G E E V F C I N G D L K Met T N
Stop

FIG. 4 a)

SEP protein 3 (SL-1469)

Nucleic acid sequence

```
AGAAATTGAAATCTCACTAAGATTTAATACTTCTCCCAATGGTGAGCGTTTATATT
TCAGAGGTAGAAAATGGGCTCTTACTGGTATCGTCAAAGCCAAAGGAGAACCAC
AAGATAGGGTATACAAAATTATTTTGGGACATGAATTCACTCCTGGATACATTGA
GAATCGTCTCAAGTTTAGAATGCAAAGAGTTGCAGTCCCTGGGCTTTTGTCTGA
TTATTCTATTTGCTTTAATATGGAAAACAAGTACCCAGACTTTGGAGAAGAGTTTA
TGACTTATGACAAGAGCACTCAATTAAAAATGTCTGGAAATGCAAGACTTCAATA
TGGTGCTGCTGCAGACTGTGACTCTACTCCTGGAGAAATGAAATTAAGCTTCGA
ACATGAAACAACTGAAGAAGCAAGAGAGGCTATGAAACACACGTGGTACTATGA
AAAGTGTATGGAACAGAAGCAACATCCAGAATGGGCAAGCAGAGGTGACAGAC
TTCCATTCACAGAAGCCTGCCACATGACAACATGGGATGCAACTACTGCTCCGT
AAATACACATGGAAGATGAACTTTGTTNAGATGACTGATCGCATTGAATGCTATT
GTTTC
``` b)

Amino Acid sequence

-E I E I S L R F N T S P N G E R L Y F R G R K W A L T G I V K A K G E P Q D R V Y K
I I L G H E F T P G Y I E N R L K F R Met Q R V A V P G L L S D Y S I C F N Met E N
K Y P D F G E E F Met T Y D K S T Q L K Met S G N A R L Q Y G A A A D C D S T P G
E Met K L S F E H E T T E E A R E A Met K H T W Y Y E K C Met E Q K Q H P E W A
S R G D R L P F T E A C H Met T T W D A T T A P stop

FIG. 5 a)

Adhesion protein 2
~Mussel adhesive plaque matrix protein 2 precursor (foot protein 2)
(mb3a02.ckr)

Nucleic acid sequence

```
TACATGTCTTGAACCTGTCTGTCCATCTAATTTGTGTAAAAATGGTGGAAAATGT
AAAGTTTATCGTGGAGTATGTTATTGCGATTGTAAAGGTACTGGTTTTGAAGGTT
CAAAATGTCATCAACCAACTTGCACACCTACAACATGTCCTAAAAATGCTGTTTG
TGAACTGGATTGGTCTAATAAAAAAACACGTCGTACATGTAAAAAAGGATTTGCT
GGTGCAAATTGTGCTGATAATGCTTGCTCCCAGTTTCCATGTGAAAATGGATCT
GAATGTGTTGTAAAATATGGATCTCAACCACAATGTGATTGTAAGCCTGGATTTT
TTGGCAATTTCTGCCAATCACATTTTTGTGAACATTTCAAATATTCAGCTGTAGGT
GGTAAATGTGAAATTATGGAAGACGAAAAAAACTTGGGAGTCTATAAACCTGTTT
GTAAATGTTTAGAAGGATATGAAGGTAAAATTTGCAGCGAAATTTCTTGCTCTGA
ATCATTCTGTCATTATCGAGGAAAATGTTCCGTTAGTAAAGATATAAGAAGCTGC
AAATGTGACAGAGGAATTCAAGGCGAGCGCTGTGAACATCCTAAACCTTGTGAA
AGTTGCGACAAAGCAGATTGTGTTAGAGAAAAACCTGGCAGTGGCAATTTTGTT
TGTGCAAAAAAATAGACATAATATAATTAAG
``` b)

Partial Amino Acid sequence

Adhesion protein 1
~Mussel adhesive plaque matrix protein precursor (foot protein 1) (sl-0927-9)

Nucleic acid sequence

CCCATCCAAAGTAGCCTCAAAAACAAAGTCATATACCCGCCCTCTTTACTCCAAA
AAGAACTTCTTACGCAAGAAACCCTCTGTATATTACAAAGTTAAGAAAAATCCCG
TCAAGTTAAGAAAAGTTAAGAAAATTCTGAGACCTGTGAGTTACTCAACTCCTCA
GACTCATCCGAGCAGCACGACTGTTTCAACCACAAGAGACTATCCAAGTAAATC
TCTTGAAAGTTTAACGCAAACTAAGAGTCCAGAAATAGTATCGGCCTTTACTCCG
GTCTCAGTCTCAAAAAAGTCTATTAAATCATTGAATGCTCGAAAATCCATTTATGC
AAGTCCATCTACCCCATCTTTTAGATATTCACCAACAACACCTTCTTCATATCAAA
GTCTTAAGCCATTTGAGCCCAAACCTATTCATAGATTCAGATCTAAGCCAGGCTA
CAAGTCTACCAGATCCAAACCTACTTATGTTTCGTCAACGACCACCCACCCAGC
GTATGTATCATCTACTATTAGTCCAGCCTATGCATCATCTAGTGTTAGTCCAGCC
TATGCATCATCTAGTGTTAGCCCAGCCTATGCATC b)

Amino Acid sequence

PSKVASKTKSYTRPLYSKKNFLRKKPSVYYKVKKNPVKLRK
VKKILRPVSYSTPQTHPSSTTVSTTRDYPSKSLESLTQTKSPE
IVSAFTPVSVKKSIKSLNARKSIYASPSTPSFRYSPTTPSSYQ
SLKPFEPKPIHRFRSKPGYKSTRSKPTYVSSTTTHPAYVSSTI
SPAYASSSVSPAYASSSVSPAYA

FIG. 7 a)

Cuticle binding protein 1
~BCS-1 like protein (moran 9-15)

Nucleic acid sequence

AGCGTGGTCGCGGCCGAGGTACGCGGGGAATCAGTACAAAGTTTACAGGCAAC
AATGATCATGTACACCTCAGTATTCCTTCTTTCCATCGTCTTTTCATGTGCCTTTG
GAGCACCCCAATATCAAGCCTCTCAGCCTGCTTATGCTCCAGTTGAAGAGCCTT
ACGCTTATCAATACGCCGTTCAAGATCCCCAATCAGGAAATGACTTTTCTGCCG
AAGAATCCTCTGATGGACAAGTCATCTCTGGATCCTATCAAGTGGCTCTCCCCG
ATGGTCGTATTCAAACTGTGACCTACACTGTGAGTGGAGATAGTGGATACGTTG
CTGATGTTCAGTATGAAGGAACTCCATCCTATCCCGAAGCTCCTCAGCAACCCA
GATATGTTTAAAAAGTTTGGCATTGATGAATATTCATTAATTGATTTATATTTATGT
TAAATATATTATTCATAGTTGAAATTGATATTGTTTACTCTCAAAGAAATACAAATT
TATATTTATATTTT b)

Amino Acid sequence

Vitellogenin-like protein SL-903  >SL0903FLG

```
TATTCCAACGTAACATGATCAGAGGATGGGCTCAAAGACTCCAATTGAACATGGATAAAATCAACAATCATGGAC
ATGGATTCCATTCTGAAGAGCAATCCATCTTTGGAGATTGTGATACTCTTTACACTGTTAGTGATCATAAAATTGTG
AAATCTGTAAGTCATACTAAAGATTGCAAAAACAGAGTACGTGTCCTCATTGATGATTGGAGGGGCGAACGCTGT
GACATTGACCCAGAGCATCCAGAAAGCAGAGAAAATCCAAATGGTCTTTACTCTGCTTCCAACACCATTTATGTCG
TGGACAAGAAGGGAGATCATTTCCACCCTAAGGCCATCATTGGATCATCCTCAGTTGTTGCACAATTCTATCAAAT
GGAAGGAGTCTCCTTTATTGCTCACTCTAATTCAACATCTATTTTGAAATCTGTTGAAGATATCTCAGAACCTATGG
TTGTTGTTGGAATCCCAGTCAAGGATCTCAAATACGAATTTGAAGATAAAGAATATCAATGGAATTCTGACAGAG
ACCTCAAGGCTCGTGAAGAACATTTATCCACTGGTGAATTTTTTGAGAGTGACATGTCCACTTTGTCAAAATATGT
TAAGGAAAAGCTCAACAAGTTCCATGACATCATGCAACATCTTTCAAATGACAAAGATGCCATTGCAGAAGCTCA
TGATAATGGAGTAAACAGTATGGTACCCGGTATGTTGGCTATGGACTACAATACATTGAAGGCTATGTCTGAAGA
ACTTCACTCAGACAAATCTGATGAAGGTGTATTCAAATACAATCTTTTCAATGAACTTTTGGGAAGTTTAGGAACC
AGCGCTTCTGCACTCCTGGTCCGTGACATGATCATGGAAGACAAATTTGAAAACTTCAGGGATGCTGTCCGTGCTC
TTACTGCCATTCCTTTCCATATTCGTCACCCTAACAAGCAACTTTTGAGTGAATTCGAAGCTTTGTACAACTACGAT
GGAGATCAACTCCTCAAAGATGCCGTCCCAATTGTTCTTGGACACTTAGCACGAGTTACCTGCGAAAGAGCCGGA
GTAATGCACTCCCCTGCTTCTAAAGAATGTTTCCACTCTGTTGTCGATGGATACGCCGATAAAACAATTGAAAAAA
TTATGGGTGCATCTGACCACAAAGAGCAAATTAAGCTTCTTGGAATGTTGTTCAATCTTCGCTATGGAAACGTTGC
TGAAAAATTAAAGCCTCTTATTTATGGAGAAACTGAGATCAAATGTGGACATCTCCGTACTCTTGCTGTTCAAGCT
GCTGCTTTTGGAGCAATCAACAACGGAAAGGGAGCTGAATATTTATTGCCCATTTTTGCGGACAGTGAAAACTCTC
ATGAACTTAGATTGACAGCTCTCTCATACTTGATGGATGCTCATCCCACCGCAACTCACTTTAACACCATCGTTGCT
GTACTTTACAGAGAAAAAGATTATGAAGTTATCAACTATGCTTTTACACTCTTGGATAAATATGCAACCAATATTA
ACCCCTGCAAAAAATCGGTCTCTGTATTGGCCAAATACTTCTTGAAATATCTTAAGCAATACAGTCATTTTGAAAC
TGACTATGGATTGGGAGTGTCCAAAACTTATAGTCGTCAATTCCAACAATCTAAATACGGGTATGGAGGTGAATAC
AGCTACTGGGTCATTGGATCTCATAGTTCTACCCTTCCTCTGAGTGTTGCAATGTGTATGGACACAACCTTGTTTGG
AGGATATACCGCTAATGGAATGTGTGTGCAATTAAGAATTGAAGGATTGTCCAAGGCTCTCATCCGTAAATTCAAG
ACGATGAGCCCAGATATCTGGAAATCTGAAGATCTCAAAAGTATCTTAATGGGAGATATGAACATTAAGGAAAGA
CCTGATCAACCAATCAACGTTGAGGTTCTCCTTTTCGTCAAGAACTCAGTTGTTGCATTCAGACAATATAACGAAG
ATTCAATTAAGGAAGGTGGGAACTTGAAAGAAATTTTCGATCGATTGAAAGGACTTGGAGACACCTACTCCATTA
ATCACCAAAGAGCAATGAGATTTGGAAGCCTCTTGTACCAACAACCCTTGGAAGTCGGTGCTCCAGTCTCTTACTT
AAACTCATTCACCGGCGTTTTTGATGTTCAAGCTACAATTAAGAAGGGAAATGCCAGAGGTCTTATGTTCAGAGAT
GTCAAATATAACATGAACTTTTTTGGACATGGATCTCGTATGATGATGGTTCAAAACCCACAATCAAAGATGTTTT
ATTCCATTTCTCAAAACCGCATTTATGGCTCCCATTTCCCAAGAGAATTTGTCATTGGAGTTAATCCATTGAAGAAA
GAGTTTAAATTATCTATTCAACGGCCTTCTTATGAGAATCCACTCGTACTTATGATGCACTCTTTAACAAAAGTTTA
CACTGGATCTCAAAATGTTAATGAAAAGCAGGATATTTCAGCCAACTGTCCTGAGTGCAAGTCTGATACTCCTGTA
TCGTATGGTCCAGATGCTGCTAAAACCAGAGTCTTTTTAAACCATGATTGCGATAAGACTGGCTCTTATATTCACG
GGGAATACTTTGACTGTGAAATGGAATCCAATAGGGGAAAGGTCTTATACCATTTGTGGAGAGCCATGTTACCTTA
TAACAAAAACCCTAAGACCTTTGGAAATGGTATTCGCATGGGTATTCGTCAAATCAGAGCTTATTTTGTTTTCTTCC
CAAGAGCTGAAAAATGTGGAGCAATGCTTCGCTGGTCACAATCAAAGGAAAATCCAGTTAAAGAGCTTGAAATTT
CTATGAGATTCAATGCTAATCCCAATGGCGAGCGTCTTTTCTTTAGAGGACGTAAATGGGTAGTCACAACTATTAT
CAAAGCCAAAGGAGAACCACAAGATAGGGTATACAAAATTATTTTGGGACATGAATTCACTCCTGGATACATTGA
GAATCGTCTCAAGTTTAGAATGCAAAGAGCTGCAGTTCCTGGAATTATGTCTGATTATTCTATTTGCTTCAATATGG
AAAACAAGTACCCAGACTTTGGAGAAGAGTTTATGACTTATGACAAGAGCACTCAATTAAAAATGACTGGAAAGG
CAAAACTTCAATATGGTGCTGCTGCAGACTGTGACTCTACTCCTGGAGAAATGAAATTAAGCTTCAAACATGAAAC
AACTGAAGAAGCAAGAGAGGCTATGAAACACACTTGGTACTATGAAAAGTGTATGGAACAGAAGAAACAGCCAG
AATGGGCAAACAGAGGTGATAAACTTCCATTCACACAAGCTTGCCACATGACAACATGGGATGCAACTACTGCAC
GTAAATACTCATGGAAGATGAACTTTGTTAAGATGACTGATCGCATGAATGCTATTGTTTCTCAATTCCAAAGTAT
CATGAAAACTGGTCTTTTACCTTACTGGGACATTGATCCAGAAATTATCCCAGCTACAAGTGCTGATCCCCACATG
AATATCAAAGCTACCCTTAAAAACCACGACAAGAATGTTGATATGTACATGGAAACCAGTCAGGGAGGTCAACGT
TTCAACGATATTCCTCTTAGTTTAAATTGGCGCCCAATGTTGAGAAACCTTAAGTTTACATCCACCACTAGACGTCT
CATGCAATACAAAATTATCCATGGATGTACTACCACAATTGACCATGTATATACTCTTGACAATGTCACATATCCT
TACACACCTACCTCATGCTGGACGTTGGCTTCTGGACACTGTTCCCCACATCCAACTTATGCAGTTTTTGTCAAAAA
GTCTGCAGGATCTCATTTAGATGCTAAAATTTATTTGGGCGGTCACAGCATCGAATTCCAAACAAGTGGCCCAAAG
AAGATTAATGTTCTCATCAACGGTGAAGCTATTGATGTAGGAGAGGAGGAACATGTTCATGAACAAGACGGACAA
GAAATTTTCAAGGTCTTAAAATGGGGATCAAGTTACAGTGTTTACTCCTTCTTGAAAATCTGGGTAGTCTATGATG
GCCATGCAGTCAGCTTAATCCCTGCTCCATCTGTTACGGGTCAACATTGCGGTTTGTGTGGAAACTTCAACAGAAA
CCAATATGATGAATTTGAAAGCAAGGATGCTCATCAATTGAAGACATCCGACGAGCTTGTTGAAGATTATAAATG
GAAGTGT*TGA*GAATTTATTTCTTTCATCG
```

FIG. 12

SEP protein 1 SL-0547
>SL0547DRFL

CTTCTTAAATCCTGAAAAGGTAGTAGTAGAACTTCCACGGAAATGGCGAA
GAACAAGAACGTCGGTAAGCCGAGGAACTACAAGTTAGCCTCCGGAGTC
GTCCGGTTCGGCAAATCTAAAATGTACCACAAGAAGGCAATCTATAAATT
CTTGAAGAAGACAACTCCCAAAAAGGTTGAGGCCAGTAAGCCCGCCTTCG
TTGAGAAGAAGGTCGGAGGTGCCAAGAATGGGGGTACTCGTATGGTTCGC
GTCAAGAAGTTGAAGAACGACTTCCCCACCATGGAAAGACGTGCTCATAG
AATCGCCAAGAAGCCTGAAAAGCTCTCTCGCAGGGTCCGTCCTACCCTCA
CCCCTGGAACTATTGCAGTTATTCTTGCAGGTATCCACAAAGGAAAGAGA
ATCGTCATTCTCAAGGAGCTCTCCAGTGGAATGCTTCTGATTTCTGGCCCC
TTCAAGCTTAATAACTGCCCAATTAGAAGGATTAATCAACGCTATTTGTTG
GCCACATCAACCAAGCTCGATGTTTCATCCATTAAAATGCCCGAGAACAT
TAATGATGATTACTTCCGTCGTTTAAGAGCCGCCAAGAAGCCAGCTGGTA
GTGTATTCGAAGGTAAAAAGGAAGAATACAAACCTTCTGAACAACGTAAG
AAGGACCAAGTCGAAGTTGATAAGCAGCTCCTCAATGTCATCATGAAGCA
CCCCGAAGCCTCTCTTTTGAAACAATACTTGAAGAAGTCCTTCGGTCTTAG
CAAGGGACAATATCCTCATAATATGAAATTT*TAA*TTGTCGTCTTGTTAAAT
AAAACTAAAATTCCTCGC

FIG. 13

SEP protein 2 SL-0858
>SL0858C4

TCAATTTGATTGATCCAGGAAGAGAAAC<u>ATG</u>AAGATCATTGCCATCTTTG
CACTTTTGTTCATTGCCGTGTCTGGAGAGGATCTGGAGTGGGAGTCCTGCA
ATCCCGATAACTTGGGAGAAGGAGACATTGCCCTCTCTCCTTATCCCCTTC
CAGTAGTTAGTGGAACCAGTCTGGATTTGAAAGCCCTCTTTGATCTTCACA
AGGACCTCGATGGAGATGTGGATGTTGAACTCAAGTTGGTCAAGAAAGGA
ATTGTCTCCATTCCCATCCCCTGCATTGAAAGCCCTTCAGGCCTGCATTTG
GGCTCTTGTTCCTACAAACTGGAGGAGATTGTCAGCAAATATGCGTATTTC
TTGTGTCCAGACTATTTTCCAGAGGGCCAAAGCTGTTCTTTCCCTTTGAAG
GCAGGACAATATGGAGGTGAGATCTCTGGTATTGTTCTACCTGACATCCC
ACCTTCCATTTCCAACCTCGCCAAGGGAACCATTCATGGAACTCTCTCTGT
GACCAGAAACGGGGAAGAAGTTTTCTGTATCAATGGAGATTTGAAAATGA
                    CAAAT<u>*TAA*</u>TCCTTGTTTCTGTATCC
ATATTTGAA

FIG. 14

SEP protein 3 SL-1469
>SL1469FLRD

```
CCATTCAAGATGAGAGTCACAGCCCTCCTTTGCTTATTTGTTGCCGCTGTCAGCGGAAGCATATTTGAAGATGGAA
AGCAATATGTATTTGATTCAGAGACATCTGTTGTTGTTGGTACGATGGACCATGCTCCACACTCATCTGGATTTGC
TTACAAGCACCATACTACCATGCAAGTTCAAGGAGATAACATCAAAGTGAAGCTTTCTGACGTTGAATTCTCACAA
TTCAATGGAAAACATGAGAATGGAGAGTTCCCATTTGACCACACTAACTTTGTTGCAACAAACAGAGACATTCCTG
CATTTGAAGTTCAGTTGGACTCCCATGGATTGTTTTCATCCCTCAAAGTTGGTCCTAAACTGACACTATTCCAACG
TAACATGATCAGAGGATGGGCTCAAAGACTCCAATTGAACATGGATAAAATCAACAATCATGGACATGGATTCCAT
TCTGAAGAGCAATCCATCTTTGGAGATTGTGATACTCTTTACACTGTTAGTGATCATAAAATTGTGAAATCTGTAA
GTCATACTAAAGATTGCAAAAACAGAGTACGTGTCCTCATTGATGATTGGAGGGGCGAACGCTGTGACATTGACCC
AGAGCATCCAGAAAGCAGAGAAAATCCAAATGGTCTTTACTCTGCTTCCAACACCATTTATGTCGTGGACAAGAAG
GGAGATCATTTCCACCCTAAGGCCATCATTGGATCATCCTCAGTTGTTGCACAATTCTATCAAATGGAAGGAGTCT
CCTTTATTGCTCACTCTAATTCAACATCTATTTTGAAATCTGTTGAAGATATCTCAGAACCTATGGTTGTTGTTGG
AATCCCAGTCAAGGATCTCAAATACGAATTTGAAGATAAAGAATATCAATGGAATTCTGACAGAGACCTCAAGGCT
CGTGAAGAACATTTATCCACTGGTGAATTTTTTGAGAGTGACATGTCCACTTTGTCAAAATATGTTAAGGAAAAGC
TCAACAAGTTCCATGACATCATGCAACATCTTTCAAATGACAAAGATGCCATTGCAGAAGCTCATGATAATGGAGT
AAACAGTATGGTACCCGGTATGTTGGCTATGGACTACAATACATTGAAGGCTATGTCTGAAGAACTTCACTCAGAC
AAATCTGATGAAGGTGTATTCAAATACAATCTTTTCAATGAACTTTTGGGAAGTTTAGGAACCAGCGCTTCTGCAC
TCCTGGTCCGTGACATGATCATGGAAGACAAATTTGAAAACTTCAGGGATGCTGTCCGTGCTCTTACTGCCATTCC
TTTCCATATTCGTCACCCTAGCAAGCAACTTTTGAGTGAATTCGAAGCTTTGTACAACTACGATGGAGATCAACTC
CTCAAAGATGCCGTCCCAATTGTTCTTGGACACTTAGCACGAGTTACCTGCGAAAGAGCCGGAGTAATGCACTCCC
CTGCTTCTAAAGAATGTTTCCACTCTGTTGTCGATGGATACGCCGATAAAACAATTGAAAAAATTATGGGTGCATC
TGACCACAAAGAGCAAATTAAGCTTCTTGGAATGTTGTTCAATCTTCGCTATGGAAACGTTGCTGAAAAATTAAAG
CCTCTTATTTATGGAGAAACTGAGATCAAATGTGGACATCTCCGTACTCTTGCTGTTCAAGCTGCTGCTTTTGGAG
CAATCAACAACGGAAAGGGAGCTGAATATTATTGCCCATTTTTGCGGACAGTGAAAACTCTCATGAACTTAGATT
GACAGCTCTCTCATACTTGATGGATGCTCATCCCACCGCAACTCACTTTAACACCATCGTTGCTGTACTTTACAGA
GAAAAAGATTATGAAGTTATCAACTATGCTTTTACACTCTTGGATAAATATGCAACCAATATTAACCCCTGCAAGA
AATCGGTCTCTGTATTGGCCAAATACTTCTTGAAATATCTTAAGCAATACAGTCATTTTGAAACTGACTATGGATT
GGGAGTGTCCAAAACTTATAGTCGTCAATTCCAACAATCTAAATACGGGTATGGAGGTGAATACAGCTACTGGGTC
ATTGGATCTCATAGTTCTACCCTTCCTCTGAGTGTTGCAATGTGTATGGACACAACCTTGTTTGGAGGATATACCG
CTAATGGAATGTGTGTGCAATTAAGAATTGAAGGATTGTCCAAGGCTCTCATCCGTAAATTCAAGACGATGAGCCC
AGATATCTGGAAATCTGAAGATCTCAAAAGTATCTTAATGGGAGATATGAACATTAAGGAAAGACCTGATCAACCA
ATCAACGTTGAGGTTCTCCTTTTCGTCAAGAACTCAGTTGTTGCATTCAGACAATATAACGAAGATTCAATTAAGG
AAGGTGGGAACTTGAAAGAAATTTTCGATCAATTGAAAGGACTTGGAGGCACCTACTCCATTAATCACCAAAGAGC
AATGAGATTTGGAAGCCTCTTGTACCAACAACCCTTGGAAGTCGGTGCTCCAGTCTCTTACTTAAACTCATTCACC
GGCGTTTTTGATGTTCAAGCTACAATTAAGAAGGGAAATGCCAGAGGTCTTATGTTCAGAGATGTCAAATATAACA
TGAACTTTTTTGGACATGGATCTCGTATGATGATGGTTCAAAACCCACAATCAAAGATGTTTTATTCCATTTCTCA
AAACCGCATTTATGGCTCCCATTTCCCAAGAGAATTTGTCATTGGAGTTAATCCATTGAAGAAAGAGTTTAAATTA
TCTATTCAACGGCCTTCTTATGAGAATCCACTCGTACTTATGATGCACTCTTTAACAAAAGTTTACACTGGATCTC
AAAATGTTAATGAAAAGCAGGATATTTCAGCCAACTGTCCTGAGTGCAAGTCTGATACTCCTGTATCGTATGGTCC
AGATGCTGCTAAAACCAGATGTCTTTTTAAACCATGATTGCGATAAGACTGGCTCTTATATTCACGGGGAATACTTT
GACTGTGAAATGGAATCCAATAGGGGAAAGGTCTTATACCATTTGTGGAGAGCCATGTTACCTTATAACAAAAACC
CTAAGACCTTTGGAAATGGTATTCGCATGGGTATTCGTCAAATCAGAGCTTATTTTGTTTCTTCCCAAGAGCTGA
AAAATGTGGAGCAATGCTTCGCTGGTCACAATCAAAGGAAAATCCAGTTAAAGAGCTTGAAATTTCTATGAGATTC
AATGCTAATCCCAATGGCGAGCGTCTTTTCTTTAGAGGACGTAAATGGGTAGTCACAACTATTATCAAAGCCAAAG
GAGAACCACAAGATAGGGTATACAAAATTATTTTGGGACATGAATTCACTCCTGGATACATTGAGAATCGTCTCAA
GTTTAGAATGCAAAGAGCTGCAGTTCCTGGAATTATGTCTGATTATTCTATTTGCTTCAATATGGAAAACAAGTAC
CCAGACTTTGGAGAAGAGTTTATGACTTATGACAAGAGCACTCAATTAAAAATGACTGGAAAGGCAAAACTTCAAT
ATGGTGCTGCTGCAGACTGTGACTCTACTCCTGGAGAAATGAAATTAAGCTTCAAACATGAAACAACTGAAGAAGC
AAGAGAGGCTATGAAACACACTTGGTACTATGAAAAGTGTATGAACAGAAGAAACAGCCAGAATGGGCAAACAGA
GGTGATAAACTTCCATTCACACAAGCTTGCCACATGACAACATGGGATGCAACTACTGCTCCGTAAATAC
```

FIG. 15

(mussel adhesive protein) SL-0927
>SL0927R61

CCAATTCTAGC*TAG*TCACTA*TGA*ACTAGTCAAAATAATTTATATACTGTTTTTATA
TTGATTTTTATTTATATATTATTACATCCT*TGA*GGACTTTTGAACAAAGGTGTTCGT
AGTAAACTTTTGAGTCATTATTACATAGTTGTCATACCTATTTCAAGGATAATAAG
GACGATCATC<u>ATG</u>AAAACATCTATTATTTTCTCACTGTATGTTCTGCCTTCTATAC
TGCACCTTGCTGTAAGTGAAGATAAAACTATTATAGCTGAAGACCTGACAGCTGT
AGAGTCACGCTATAAAGTAGATGCAAAACCCTCACCTTATGTTCCTCCACAACCA
GCACCAGATTTTGATTACTTTGCACCCACTGTATCTCCTTCTTTCTCCCAATCGC
ATCTCCCTCTCCTTCTTCCCTGTTACATCCTACTTTACACCCACAACCATTCCTCC
AGTGACTCCCTCGACCACAACGACCACTGTTACAACAACAACCCCTGCCACATCT
ACTTACAGAAAGTTATTCTTTCCAACGTCTTTCAAACCATCTTTTCTTTCTTCTCGA
AAAAAGTTAACCACAACTACAACAACGCCGGCTACAACATCCTCAACAACAACA
ACAATAACCTTCACCCCAACTACTTCACCCCCTCCATCTGCTAATGAAGTTCGAA
CAACATTAAACCCATCCAAAGTAGCCTCAAAAACAAAGTCATATACCCGCCCTCT
TTACTCCAAAAAGAACTTCTTACGCAAGAAACCCTCTGTATATTACAAAGTTAAG
AAAAATCCCGTCAAGTTAAGAAAAGTTAAGAAAATTCTGAGACCTGTGAGTTACT
CAACTCCTCAGACTCATCCGAGCAGCACGACTGTTTCAACCACAAGAGACTATCC
AAGTAAATCTCTTGAAAGTTTAACGCAAACTAAGAGTCCAGAAATAGTATCGGCC
TTTACTCCGGTCTCAGTCTCAAAAAGTCTATTAAATCATTGAATGCTCGAAAAT
CCATTTATGCAAGTCCATCTACCCCATCTTTTAGATATTCACCAACAACACCTTCT
TCATATCAAAGTCTTAAGCCATTTGAGCCCAAACCTATTCATAGATTCAGATCTA
AGCCAGGCTACAAGTCTACCAGATCCAAACCTACTTATGTTTCGTCAACGACCAC
CCACCCAGCGTATGTATCATCTACTATTAGTCCAGCCTATGCATCATCTAGTGTTA
GTCCAGCCTATGCATCATCTAGTGTTAGCCCAGCCTATGCATCCACAACAGTTAA
ACCTGTCTTTGTTTCTACGACAGCAAATGAAATATACTATACGCCCGAACCAAAA
AGGGTACGAAGTCTTCCACTTACACGAGAACAAGCACATCTCTATTCATCTATTC
CTTATGATTCAACAACTACATCAAGGCAGCCTCCAGCTCCTGTTTCCTACAGTAC
ACCTAAGCCCCACTCGAAACAACATAGCCAATATCGCGAATTGCCATTGACTAGA
GAGCAAAGTGAAAACATTGAGTTTAGTACTCCCGTAAAGGCTAATACGAAGCCTT
ACAATAATAATATACAATTTAATCCTGTAAGACGGATTCCTTCTCATTATAGAAA
TCATCAAGCGTTGAATGAAATACGTCGGGAGGAAAAGTATCCTGCACAACCCTAT
TCCTTCAGCTATGATATCAAAGATGAGACAAGTGGAACGGATTTTTTCCGCTCTG
AAGAAAGCTCAGGCCCTGTGACGAAGGGAAGTTATAAGGTGGCTCTTCCTGATG
GTCGTATTCAAATTGTTGAATATATTGCAGATGAAAATGGCTATAAGGCCACAGT
TTCCTATGAGGGAGAAGCTGTTTTCCCAAATCCAGATGATTTTGAAGAAGAACCA
ACTCGGAGAACTTTTAGACACTCAAGAAAGTCGATATTGACTCTGTACCCAATA
ACAACTACTCATTTTTGCGGAATAGAGTCCGTGGTGCAGGGACTACAGAAAAAG
CTCCTTCTCCTCAAGACACAACCATTCGTCCAGTCAGTCTTCCATTAAGACATCGA
TTATCTCGTGCCGAAGTCTCAAAATCACTTCNTACGAGTCCGTTTCCTTATGCTGT
GAGTAGTACGTCACCAGCTCCATTACCTTCTAGTCAAGGCCCACAACGTTTCGT
GTTCATCATTCTTCACCAAATGTTGAGGGACGAGTATTACATCACTCAACACCTC
CAGTCAGCTATTCCCAACTCCCCCAAATCGCGACAACTCAAAAACCCAGATTCCT
TCATAACGCCAATTACGAAGAAGCATTACGAGACTATGGAATTAAGGTTGATTAT
<u>*TAA*</u>TACCTTTACTTTTTGTGATCCATTTAATATGGGTTATAAATATATTTATTAGT
ACTCATTGTTTATTTATTGTAAAAGCCGTTTAGTTGTTCAGATGAAAGTG

FIG. 16

Vitellogenin-like SL-0903

FQRNMIRGWAQRLQLNMDKINNHGHGFHSEEQSIFGDCDTLYTVSDHKIVKSVSHTKDCKNRVHVLIDD
WRGERCDIDPEHPESRENPNGLYSASNTIYVVDKKGDHFHPKAIIGSSSVVAQFYQMEGVSFIAHSNST
SILKSVEDISEPMVVVGIPVKDLKYEFEDKEYQWNSDRDLKAREEHLSTGEFFESDMSTLSKYVKEKLN
KFHDIMQHLSNDKDAIAEAHDNGVNSMVPGMLAMDYNTLKAMSEELHSDKSDEGVFKYNLFNELLGSLG
TSASALLVRDMIMEDKFENFRDAVRALTAIPFHIRHPSKQLLSEFEALYNYDGDQLLKDAVPIVLGHLA
RVTCERAGVMHSPASKECFHSVVDGYADKTIEKIMGASDHKEQIKLLGMLFNLRYGNVAEKLKPLIYGE
TEIKCGHLRTLAVQAAAFGTINNGKAEYLLPIFADSENSHELRLTALSYLMDAHPTATHFNTIVAVLY
REKDYEVINYAFTLLDKYATNINPCKKSVSVLAKYFLKYLKQYSHFETDYGLGVSKTYSRQFQQSKYGY
GGEYSYWVIGSHSSTLPLSVAMCMDTTLFGGYTANGMCVQLRIEGLSKALIRKFKTMSPDIWKSEDLKS
ILMGDMNIKERPDQPINVEVLLFVKNSVVAFRQYNEDSIKEGGNLKEIFDQLKGLGDTYSINHQRAMRF
GSLLYQQPLEVGAPVSYLNSFTGVFDVQATIKKGNARGLMFRDVKYNMNFFGHGSRMMMVQNPQSKMFY
SISQNRIYGSHFPREFVIGVNPLKKEFKLSIQRPSYENPLVLMMHSLTKVYTGSQNVNEKQDISANCPE
CKSDTPVSYGPDAAKTRVFLNHDCDKTGSYIHGEYFDCEMESNRGKVLYHLWRAMLPYNKNPKTFGNGI
RMGIRQIRAYFVFFPRAEKCGAMLRWSQSKENPVKELEISLRFNANPNGERLFFRGRKWVVTTIIKAKG
EPQDRVYKIILGHEFTPGYIENRLKFRMQRAAVPGIMSDYSICFNMENKYPDFGEEFMTYDKSTQLKMT
GKAKLQYGAAADCDSTPGEMKLSFKHETTEEAREAMKHTWYYEKCMEQKKQPEWANRGDKLPFTQACHM
TTWDATTARKYSWKMNFVKMTDRMNAIVSQFQSIMKTGLLPYWDIDPEIIPATSADPHMNIKATLKNHD
KNVDMYMETSQGGQRFNDIPLSLNWRPMLRNLKFTSTTRRLMQYKIIHGCTTTIDHVYTLDNVTYPYTP
TSCWTLASGHCSPHPTYAVFVKKSAGSHLDAKIYLGGHSIEFQTSGPKKINVLINGEAIDVGEEEHVHE
QDGQEIFKVLKWGSSYSVYSFLKIWVVYDGHAVSLIPAPSVTGQHCGLCGNFNRNQYDEFESKDAHQLK
TSDELVEDYKWKC

BLAST hits:
tr  Q9NDN7  _TENMO Melanization-related protein [160 kDa MRP] [Tene... 147 2e-33
tr  O17428  _9HYME Vitellogenin [Pimpla nipponica]         73 4e-11

FIG. 17

SEP protein 1 SL-0547
MAKNKNVGKPRNYKLASGVVRFGKSKMYHKKAIYKFLKKTTPKKVEASKPAFVEK
KVGGAKNGGTRMVRVKKLKNDFPTMERRAHRIAKKPEKLSRRVRPTLTPGTIAVILA
GIHKGKRIVILKELSSGMLLISGPFKLNNCPIRRINQRYLLATSTKLDVSSIKMPENIND
DYFRRLRAAKKPAGSVFEGKKEEYKPSEQRKKDQVEVDKQLLNVIMKHPEASLLKQ
YLKKSFGLSKGQYPHNMKF

BLAST hits:
tr Q5UAT5 _BOMMO Ribosomal protein L6 [RpL6] [Bombyx mori (Silk m... 242 6e-63

FIG. 18

SEP protein 2 SL-0858

MKIIAIFALLFIAVSGEDLEWESCNPDNLGEGDIALSPYPLPVVSGTSLDLKALFDL
HKDLDGDVDVELKLVKKGIVSIPIPCIESPSGLHLGSCSYKLEEIVSKYAYFLCPDY
FPEGQSCSFPLK<u>AGQYGGEISGIVLPD</u>IPPSISNLAKGTIHGTLSVTRNGEEVFCIN
GDLKMTN

BLAST hits:
tr <u>Q5EN79</u> _9CNID Ganglioside M2 activator-like protein [Aurelia a... <u>44</u> 0.001

FIG. 19

SEP protein 3 SL-1469

MRVTALLCLFVAAVSGSIFEDGKQYVFDSETSVVVGTMDHAPHSSGFAYKHHTTMQV
QGDNIKVKLSDVEFSQFNGKHENGEFPFDHTNFVATNRDIPAFEVQLDSHGLFSSLK
VGPKLTLFQRNMIRGWAQRLQLNMDKINNHGHGFHSEEQSIFGDCDTLYTVSDHKIV
KSVSHTKDCKNRVHVLIDDWRGERCDIDPEHPESRENPNGLYSASNTIYVVDKKGDH
FHPKAIIGSSSVVAQFYQMEGVSFIAHSNSTSILKSVEDISEPMVVVGIPVKDLKYE
FEDKEYQWNSDRDLKAREEHLSTGEFFESDMSTLSKYVKEKLNKFHDIMQHLSNDKD
AIAEAHDNEVNSMVPGMLAMDYNTSKAMSEELHSDKSDEGVFKYNLFNELLGSLGTS
ASALLVRDMIMEDKFENFRDAVRALTAIPFHIRHPSKQLLSEFEALYNYDGDQLLKD
AVPIVLGHLARVTCERAGVMHSPASKECFHSVVDGYADKTIEKIMGASDHKEQIKLL
GMLFNLRYGNVAEKLKPLIYGETEIKCGHLRTLAVQAAAFGAINNGKGAEYLLPIFA
DSENSHELRLTALSYLMDAHPTATHFNTIVAVLYREKDYEVINYAFTLLDKYATNIN
PCKKSVSVLAKYFLKYLKQYSHFETDYGLGVSKTYSRQFQQSKYGYGGEYSYWVIGS
HSSTLPLSVAMCMDTTLFGGYTANGMCVQLRIEGLSKALIRKFKTMSPDIWKSEDLK
SILMGDMNIKERPDQPINVEVLLFVKNSVVAFRQYNEDSIKEGGNLKEIFDQLKGLG
DTYSINHQRAMRFGSLLYQQPLEVGAPVSYLNSFTGVFDVQATIKKGNARGLMFRDV
KYNMNFFGHGSRMMMVQNPQSKMFYSISQNRIYGSHFPREFVIGVNPLKKEFKLSIQ
RPSYENPLVLMMHSLTKVYTGSQNVEKQDISANCPECKSDTPVSYGPDAAKTRVFL
NHDCDKTGSYIHGEYFDCEMESNRGKVLYHLWRAMLPYNKNPKTFGNGXRMGIRQIR
AYFVFFPRAEKCGAMLRWSQSKENPVKELEISMRFNANPNGERLFFRGRKWVVTTII
KAKGEPQDRVYKIILGHEFTPGYIENRLKFRMQRAAVPGIMSDYSICFNMENKYPDF
GEEFMTYDKSTQLKMTGKAKLQYGAAADCDSTPGEMKLSFKHETTEEAREAMKHTWY
YEKCMEQKKQPEWANRGDKLPFTQACHMTTWDATTAP

BLAST hits:

tr Q9NDN7_TENMO Melanization-related protein [160 kDa MRP] [Tene... 137 1e-30
Melanization-related protein [160 kDa MRP] [Tenebrio molitor (Yellow mealworm)]
sp P18948 VIT6_CAEEL Vitellogenin 6 precursor [vit-6] [Caenorhab... 67 2e-09
tr Q7KPP7_CAEEL Vitellogenin structural genes (Yolk protein gene... 67 2e-09
tr Q8JIF9_9GOBI Vitellogenin [Vg-530] [Acanthogobius flavimanus] 66 4e-09

FIG. 20 mussel adhesive protein SL-0927

MKTSIIFSLYVLPSILHLAVSEDKTIIAEDLTAVESRYKVDAKPSPYVPPQPAPDFD
YFAPTVSPSFSPIASPSPSSPVTSYFTPTTIPPVTPSTTTTVTTTTPATSTYRKLF
FPTSFKPSFLSSRKKLTTTTTTPATTSSTTTTITFTPTTSPPPSANEVRTTLNPSKV
ASKTKSYTRPLYSKKNFLRKKPSVYYKVKKNPVKLRKVKKILRPVSYSTPQTHPSST
TVSTTRDYPSKSLESLTQTKSPEIVSAFTPVSVSKKSIKSLNARKSSYASPSTPSFR
YSPTTPSSYQSLKPFEPKPIHRFRSKPGYKSTRSKPTYVSSTTTHPAYVSSTISPAY
ASSSVSPAYASSSVSPAYASTTVKPVFVSTTANEIYYTPEPKRVRSLPLTREQAHLY
SSIPYDSTTTSRQPPAPVSYSTPKPHSKQHSQYRELPLTREQSENIEFSTPVKANTK
PYNNNIQFNPVRRIPSHYRNHQALNEIRREEKYPAQPYSFSYDIKDETSGTDFFRSE
ESSGPVTKGSYKVALPDGRIQIVEYIADENGYKATVSYEGEAVFPNPDDFEEEPTRR
TFRHSRKVDIDSVPNNNYSFLRNRVRGAGTTEKAPSPQDTTIRPVSLPLRHRLSRTE
VSKSLPTSPFPYAVSSTSPAPLPSSQGPQRFRVHHSSPNVEGRVLHHSTPPVSYSQL
PQIATTQKPRFLHNANYEEALRDYGIKVDY

BLAST hits:

tr Q9V918 _DROME CG9036-PA (RE26879p) [CG9036] [Drosophila melano... 76
2e-12 tr Q5R283 _DROSI CG9036 [Drosophila simulans (Fruit fly)]     76 2e-12 tr Q5R279 _DROSE CG9036 [Drosophila sechellia (Fruit fly)]    76 2e-12 tr Q5TRT2 _ANOGA ENSANGP00000029010 (Fragment)
[ENSANGG0000002361... 75 4e-12 tr Q9V6T6 _DROME CG6305-PA (GH20904p) [CG6305] [Drosophila melano... 74
1e-11 tr Q7QGL7 _ANOGA ENSANGP00000018947 (Fragment)
[ENSANGG0000001645... 70 2e-10 tr Q9V7U0 _DROME CG15920-PA, isoform A [CG15920] [Drosophila mela... 70
2e-10 tr Q9NDT7 _BALAM BCS-1 [bcs-1] [Balanus amphitrite (Barnacle)]     61 8e-08

SEQUENCE LISTING

```
<160> NUMBER OF SEQ ID NOS: 34

<210> SEQ ID NO 1
<211> LENGTH: 594
<212> TYPE: DNA
<213> ORGANISM: Lepeophtheirus salmonis

<400> SEQUENCE: 1
gcaatacaaa attatccatg gatgtactac cacaattgac catgtatata ctcttgacaa      60
tgtcacatat ccttacacac ctacctcatg ctggacgttg gcttctggac actgttcccc     120
acatccaact tatgcagttt ttgtcaaaaa gtctgcagga tctcatttag atgctaaaat     180
ttatttgggc ggtcacagca tcgaattcca aacaagtggc ccaaagaaga ttaatgttct     240
catcaacggt gaagctattg atgtaggaga ggaggaacat gttcatgaac aagacggaca     300
agaaattttc aaggtcttaa aatggggatc aagttacagt gtttactcct tcttgaaaat     360
ctgggtagtc tatgatggcc atgcagtcag cttaatccct gctccatctg ttacgggtca     420
acattgcggt ttgtgtggaa acttcaacag aaaccaatat gatgaatttg aaagcaagga     480
tgctcatcaa ttgaagacat ccgacgagct tgttgaagat tataaatgga agtgttgaga     540
atttatttct ttcatcgatt gatggagata tttttttacaa tgattctatt atat           594

<210> SEQ ID NO 2
<211> LENGTH: 178
<212> TYPE: PRT
<213> ORGANISM: Lepeophtheirus salmonis

<400> SEQUENCE: 2

Gln Tyr Lys Ile Ile His Gly Cys Thr Thr Thr Ile Asp His Val Tyr
1               5                   10                  15

Thr Leu Asp Asn Val Thr Tyr Pro Tyr Thr Pro Thr Ser Cys Trp Thr
                20                  25                  30

Leu Ala Ser Gly His Cys Ser Pro His Pro Thr Tyr Ala Val Phe Val
            35                  40                  45

Lys Lys Ser Ala Gly Ser His Leu Asp Ala Lys Ile Tyr Leu Gly Gly
        50                  55                  60

His Ser Ile Glu Phe Gln Thr Ser Gly Pro Lys Lys Ile Asn Val Leu
65                  70                  75                  80

Ile Asn Gly Glu Ala Ile Asp Val Gly Glu Glu His Val His Glu
                85                  90                  95

Gln Asp Gly Gln Glu Ile Phe Lys Val Leu Lys Trp Gly Ser Ser Tyr
```

```
                100              105             110
Ser Val Tyr Ser Phe Leu Lys Ile Trp Val Val Tyr Asp Gly His Ala
            115                 120             125

Val Ser Leu Ile Pro Ala Pro Ser Val Thr Gly Gln His Cys Gly Leu
        130                 135             140

Cys Gly Asn Phe Asn Arg Asn Gln Tyr Asp Glu Phe Glu Ser Lys Asp
145                 150                 155                 160

Ala His Gln Leu Lys Thr Ser Asp Glu Leu Val Glu Asp Tyr Lys Trp
                165                 170                 175

Lys Cys

<210> SEQ ID NO 3
<211> LENGTH: 508
<212> TYPE: DNA
<213> ORGANISM: Lepeophtheirus salmonis
<220> FEATURE:
<221> NAME/KEY: misc_feature
<222> LOCATION: (503)
<223> OTHER INFORMATION: n = any nucleotide

<400> SEQUENCE: 3
gtccggttcg gcaaatctaa aatgtaccac aagaaggcaa tctataaatt cttgaagaag      60
acaactccca aaaggttga ggccagtaag cccgccttcg ttgagaagaa ggtcggaggt     120
gccaagaatg ggggtactcg tatggttcgc gtcaagaagt tgaagaacga cttccccacc     180
atggaaagac gtgctcatag aatcgccaag aagcctgaaa agctctctcg cagggtccgt     240
cctaccctca cccctggaac tattgcagtt attcttgcag gtatccacaa aggaaagaga     300
atcgtcattc tcaaggagct ctccagtgga atgcttctga tttctggccc cttcaagctt     360
aataactgcc caattagaag gattaatcaa cgctatttgt tggccacatc aaccaagctc     420
gatgtttcat ccattaaaat gcccgagaac attaatgatg attacttccg tcgtttaaga     480
gccgccaaga agccagctgg tantgtat                                        508

<210> SEQ ID NO 4
<211> LENGTH: 169
<212> TYPE: PRT
<213> ORGANISM: Lepeophtheirus salmonis
<220> FEATURE:
<221> NAME/KEY: misc_feature
<222> LOCATION: (168)
<223> OTHER INFORMATION: Xaa = any amino acid

<400> SEQUENCE: 4

Val Arg Phe Gly Lys Ser Lys Met Tyr His Lys Lys Ala Ile Tyr Lys
1               5                   10                  15

Phe Leu Lys Lys Thr Thr Pro Lys Lys Val Glu Ala Ser Lys Pro Ala
            20                  25                  30

Phe Val Glu Lys Lys Val Gly Gly Ala Lys Asn Gly Gly Thr Arg Met
        35                  40                  45

Val Arg Val Lys Lys Leu Lys Asn Asp Phe Pro Thr Met Glu Arg Arg
    50                  55                  60

Ala His Arg Ile Ala Lys Lys Pro Glu Lys Leu Ser Arg Arg Val Arg
65                  70                  75                  80

Pro Thr Leu Thr Pro Gly Thr Ile Ala Val Ile Leu Ala Gly Ile His
                85                  90                  95

Lys Gly Lys Arg Ile Val Ile Leu Lys Glu Leu Ser Ser Gly Met Leu
            100                 105                 110

Leu Ile Ser Gly Pro Phe Lys Leu Asn Asn Cys Pro Ile Arg Arg Ile
```

```
                    115                 120                 125
Asn Gln Arg Tyr Leu Leu Ala Thr Ser Thr Lys Leu Asp Val Ser Ser
    130                 135                 140

Ile Lys Met Pro Glu Asn Ile Asn Asp Asp Tyr Phe Arg Arg Leu Arg
145                 150                 155                 160

Ala Ala Lys Lys Pro Ala Gly Xaa Val
                165

<210> SEQ ID NO 5
<211> LENGTH: 433
<212> TYPE: DNA
<213> ORGANISM: Lepeophtheirus salmonis

<400> SEQUENCE: 5
aagccctctt tgatcttcag aaggacctcg atggagatgt ggatgttgaa ctcaagttgg    60
tcaagaaagg aattgtctcc attcccatcc cctgcattga aagcccttca ggcctgcatt   120
tgggctcttg ttcctacaaa ctggaggaga ttgtcagcaa atatgcgtat tcttgtgtc    180 cagactattt tccagagggc caaagctgtt ctttcccttt gaaggcagga caatatggag   240
gtgagatctc tggtattgtt ctacctgaca tcccaccttc catttccaac ctcgccaagg   300
gaaccattca tggaactctc tctgtgacca gaaacgggga agaagttttc tgtatcaatg   360
gagatttgaa aatgacaaat taatccttgt ttctgtatcc atatttgaag tcaataaaat   420
acttcattaa tct                                                      433

<210> SEQ ID NO 6
<211> LENGTH: 126
<212> TYPE: PRT
<213> ORGANISM: Lepeophtheirus salmonis

<400> SEQUENCE: 6

Ala Leu Phe Asp Leu Gln Lys Asp Leu Asp Gly Asp Val Asp Val Glu
1               5                   10                  15

Leu Lys Leu Val Lys Lys Gly Ile Val Ser Ile Pro Ile Pro Cys Ile
                20                  25                  30

Glu Ser Pro Ser Gly Leu His Leu Gly Ser Cys Ser Tyr Lys Leu Glu
            35                  40                  45

Glu Ile Val Ser Lys Tyr Ala Tyr Phe Leu Cys Pro Asp Tyr Phe Pro
        50                  55                  60

Glu Gly Gln Ser Cys Ser Phe Pro Leu Lys Ala Gly Gln Tyr Gly Gly
65                  70                  75                  80

Glu Ile Ser Gly Ile Val Leu Pro Asp Ile Pro Pro Ser Ile Ser Asn
                85                  90                  95

Leu Ala Lys Gly Thr Ile His Gly Thr Leu Ser Val Thr Arg Asn Gly
            100                 105                 110

Glu Glu Val Phe Cys Ile Asn Gly Asp Leu Lys Met Thr Asn
        115                 120                 125

<210> SEQ ID NO 7
<211> LENGTH: 605
<212> TYPE: DNA
<213> ORGANISM: Lepeophtheirus salmonis
<220> FEATURE:
<221> NAME/KEY: misc_feature
<222> LOCATION: (573)
<223> OTHER INFORMATION: n = any nucleotide

<400> SEQUENCE: 7
agaaattgaa atctcactaa gatttaatac ttctcccaat ggtgagcgtt tatatttcag    60
```

```
aggtagaaaa tgggctctta ctggtatcgt caaagccaaa ggagaaccac aagatagggt      120
atacaaaatt attttgggac atgaattcac tcctggatac attgagaatc gtctcaagtt      180
tagaatgcaa agagttgcag tccctgggct tttgtctgat tattctattt gctttaatat      240
ggaaaacaag tacccagact tggagaagaa gtttatgact tatgacaaga gcactcaatt      300
aaaaatgtct ggaaatgcaa gacttcaata tggtgctgct gcagactgtg actctactcc      360
tggagaaatg aaattaagct cgaacatgaa acaactgaa gaagcaagag aggctatgaa      420
acacacgtgg tactatgaaa agtgtatgga acagaagcaa catccagaat gggcaagcag      480
aggtgacaga cttccattca cagaagcctg ccacatgaca acatgggatg caactactgc      540
tccgtaaata cacatggaag atgaactttg ttnagatgac tgatcgcatt gaatgctatt      600
gtttc                                                                 605
```

<210> SEQ ID NO 8
<211> LENGTH: 181
<212> TYPE: PRT
<213> ORGANISM: Lepeophtheirus salmonis

<400> SEQUENCE: 8

```
Glu Ile Glu Ile Ser Leu Arg Phe Asn Thr Ser Pro Asn Gly Glu Arg
1               5                   10                  15

Leu Tyr Phe Arg Gly Arg Lys Trp Ala Leu Thr Gly Ile Val Lys Ala
            20                  25                  30

Lys Gly Glu Pro Gln Asp Arg Val Tyr Lys Ile Ile Leu Gly His Glu
        35                  40                  45

Phe Thr Pro Gly Tyr Ile Glu Asn Arg Leu Lys Phe Arg Met Gln Arg
    50                  55                  60

Val Ala Val Pro Gly Leu Leu Ser Asp Tyr Ser Ile Cys Phe Asn Met
65                  70                  75                  80

Glu Asn Lys Tyr Pro Asp Phe Gly Glu Glu Phe Met Thr Tyr Asp Lys
                85                  90                  95

Ser Thr Gln Leu Lys Met Ser Gly Asn Ala Arg Leu Gln Tyr Gly Ala
            100                 105                 110

Ala Ala Asp Cys Asp Ser Thr Pro Gly Glu Met Lys Leu Ser Phe Glu
        115                 120                 125

His Glu Thr Thr Glu Glu Ala Arg Glu Ala Met Lys His Thr Trp Tyr
    130                 135                 140

Tyr Glu Lys Cys Met Gln Lys Gln His Pro Glu Trp Ala Ser Arg
145                 150                 155                 160

Gly Asp Arg Leu Pro Phe Thr Glu Ala Cys His Met Thr Thr Trp Asp
                165                 170                 175

Ala Thr Thr Ala Pro
            180
```

<210> SEQ ID NO 9
<211> LENGTH: 689
<212> TYPE: DNA
<213> ORGANISM: Lepeophtheirus salmonis

<400> SEQUENCE: 9

```
tacatgtctt gaacctgtct gtccatctaa tttgtgtaaa atggtggaa aatgtaaagt       60 ttatcgtgga gtatgttatt gcgattgtaa aggtactggt tttgaaggtt caaaatgtca     120
tcaaccaact tgcacaccta caacatgtcc taaaaatgct gtttgtgaac tggattggtc     180
taataaaaaa acacgtcgta catgtaaaaa aggatttgct ggtgcaaatt gtgctgataa     240
```

```
tgcttgctcc cagtttccat gtgaaaatgg atctgaatgt gttgtaaaat atggatctca       300
accacaatgt gattgtaagc ctggattttt tggcaatttc tgccaatcac attttttgtga      360 acatttcaaa tattcagctg taggtggtaa atgtgaaatt atggaagacg aaaaaaactt      420
gggagtctat aaacctgttt gtaaatgttt agaaggatat gaaggtaaaa tttgcagcga      480
aatttcttgc tctgaatcat tctgtcatta tcgaggaaaa tgttccgtta gtaaagatat      540
aagaagctgc aaatgtgaca gaggaattca aggcgagcgc tgtgaacatc ctaaaccttg      600
tgaaagttgc gacaaagcag attgtgttag agaaaaacct ggcagtggca attttgtttg      660
tgcaaaaaaa tagacataat ataattaag                                        689
```

<210> SEQ ID NO 10
<211> LENGTH: 223
<212> TYPE: PRT
<213> ORGANISM: Lepeophtheirus salmonis

<400> SEQUENCE: 10

```
Thr Cys Leu Glu Pro Val Cys Pro Ser Asn Leu Cys Lys Asn Gly Gly
1               5                   10                  15

Lys Cys Lys Val Tyr Arg Gly Val Cys Tyr Cys Asp Cys Lys Gly Thr
            20                  25                  30

Gly Phe Glu Gly Ser Lys Cys His Gln Pro Thr Cys Thr Pro Thr Thr
        35                  40                  45

Cys Pro Lys Asn Ala Val Cys Glu Leu Asp Trp Ser Asn Lys Lys Thr
    50                  55                  60

Arg Arg Thr Cys Lys Lys Gly Phe Ala Gly Ala Asn Cys Ala Asp Asn
65                  70                  75                  80

Ala Cys Ser Gln Phe Pro Cys Glu Asn Gly Ser Glu Cys Val Val Lys
                85                  90                  95

Tyr Gly Ser Gln Pro Gln Cys Asp Cys Lys Pro Gly Phe Phe Gly Asn
            100                 105                 110

Phe Cys Gln Ser His Phe Cys Glu His Phe Lys Tyr Ser Ala Val Gly
        115                 120                 125

Gly Lys Cys Glu Ile Met Glu Asp Glu Lys Asn Leu Gly Val Tyr Lys
    130                 135                 140

Pro Val Cys Lys Cys Leu Glu Gly Tyr Glu Gly Lys Ile Cys Ser Glu
145                 150                 155                 160

Ile Ser Cys Ser Glu Ser Phe Cys His Tyr Arg Gly Lys Cys Ser Val
                165                 170                 175

Ser Lys Asp Ile Arg Ser Cys Lys Cys Asp Arg Gly Ile Gln Gly Glu
            180                 185                 190

Arg Cys Glu His Pro Lys Pro Cys Glu Ser Cys Asp Lys Ala Asp Cys
        195                 200                 205

Val Arg Glu Lys Pro Gly Ser Gly Asn Phe Val Cys Ala Lys Lys
    210                 215                 220
```

<210> SEQ ID NO 11
<211> LENGTH: 585
<212> TYPE: DNA
<213> ORGANISM: Lepeophtheirus salmonis

<400> SEQUENCE: 11

```
cccatccaaa gtagcctcaa aaacaaagtc atatacccgc cctctttact ccaaaaagaa      60
cttcttacgc aagaaacccct ctgtatatta caaagttaag aaaaatcccg tcaagttaag    120
aaaagttaag aaaattctga gacctgtgag ttactcaact cctcagactc atccgagcag    180
```

```
cacgactgtt tcaaccacaa gagactatcc aagtaaatct cttgaaagtt taacgcaaac      240
taagagtcca gaaatagtat cggcctttac tccggtctca gtctcaaaaa agtctattaa      300
atcattgaat gctcgaaaat ccatttatgc aagtccatct accccatctt ttagatattc      360
accaacaaca ccttcttcat atcaaagtct taagccattt gagcccaaac ctattcatag      420
attcagatct aagccaggct acaagtctac cagatccaaa cctacttatg tttcgtcaac      480
gaccacccac ccagcgtatg tatcatctac tattagtcca gcctatgcat catctagtgt      540
tagtccagcc tatgcatcat ctagtgttag cccagcctat gcatc                     585
```

```
<210> SEQ ID NO 12
<211> LENGTH: 194
<212> TYPE: PRT
<213> ORGANISM: Lepeophtheirus salmonis

<400> SEQUENCE: 12

Pro Ser Lys Val Ala Ser Lys Thr Lys Ser Tyr Thr Arg Pro Leu Tyr
1               5                   10                  15

Ser Lys Lys Asn Phe Leu Arg Lys Lys Pro Ser Val Tyr Tyr Lys Val
            20                  25                  30

Lys Lys Asn Pro Val Lys Leu Arg Lys Val Lys Lys Ile Leu Arg Pro
        35                  40                  45

Val Ser Tyr Ser Thr Pro Gln Thr His Pro Ser Ser Thr Thr Val Ser
    50                  55                  60

Thr Thr Arg Asp Tyr Pro Ser Lys Ser Leu Glu Ser Leu Thr Gln Thr
65                  70                  75                  80

Lys Ser Pro Glu Ile Val Ser Ala Phe Thr Pro Val Ser Val Ser Lys
                85                  90                  95

Lys Ser Ile Lys Ser Leu Asn Ala Arg Lys Ser Ile Tyr Ala Ser Pro
            100                 105                 110

Ser Thr Pro Ser Phe Arg Tyr Ser Pro Thr Thr Pro Ser Ser Tyr Gln
        115                 120                 125

Ser Leu Lys Pro Phe Glu Pro Lys Pro Ile His Arg Phe Arg Ser Lys
    130                 135                 140

Pro Gly Tyr Lys Ser Thr Arg Ser Lys Pro Thr Tyr Val Ser Ser Thr
145                 150                 155                 160

Thr Thr His Pro Ala Tyr Val Ser Ser Thr Ile Ser Pro Ala Tyr Ala
                165                 170                 175

Ser Ser Ser Val Ser Pro Ala Tyr Ala Ser Ser Val Ser Pro Ala
            180                 185                 190

Tyr Ala
```

```
<210> SEQ ID NO 13
<211> LENGTH: 507
<212> TYPE: DNA
<213> ORGANISM: Lepeophtheirus salmonis

<400> SEQUENCE: 13
agcgtggtcg cggccgaggt acgcggggaa tcagtacaaa gtttacaggc aacaatgatc      60
atgtacacct cagtattcct tctttccatc gtctttcat gtgcctttgg agcaccccaa      120
tatcaagcct ctcagcctgc ttatgctcca gttgaagagc cttacgctta tcaatacgcc      180
gttcaagatc cccaatcagg aaatgacttt tctgccgaag aatcctctga tggacaagtc      240
atctctggat cctatcaagt ggctctcccc gatggtcgta ttcaaactgt gacctacact      300
gtgagtggag atagtggata cgttgctgat gttcagtatg aaggaactcc atcctatccc      360
```

```
gaagctcctc agcaacccag atatgtttaa aaagtttggc attgatgaat attcattaat    420
tgatttatat ttatgttaaa tatattattc atagttgaaa ttgatattgt ttactctcaa    480
agaaatacaa atttatattt atatttt                                        507
```

```
<210> SEQ ID NO 14
<211> LENGTH: 129
<212> TYPE: PRT
<213> ORGANISM: Lepeophtheirus salmonis

<400> SEQUENCE: 14
```

```
Ser Val Val Ala Ala Glu Val Arg Gly Glu Ser Val Gln Ser Leu Gln
  1               5                  10                  15

Ala Thr Met Ile Met Tyr Thr Ser Val Phe Leu Leu Ser Ile Val Phe
             20                  25                  30

Ser Cys Ala Phe Gly Ala Pro Gln Tyr Gln Ala Ser Gln Pro Ala Tyr
         35                  40                  45

Ala Pro Val Glu Glu Pro Tyr Ala Tyr Gln Tyr Ala Val Gln Asp Pro
     50                  55                  60

Gln Ser Gly Asn Asp Phe Ser Ala Glu Glu Ser Ser Asp Gly Gln Val
 65                  70                  75                  80

Ile Ser Gly Ser Tyr Gln Val Ala Leu Pro Asp Gly Arg Ile Gln Thr
                 85                  90                  95

Val Thr Tyr Thr Val Ser Gly Asp Ser Gly Tyr Val Ala Asp Val Gln
            100                 105                 110

Tyr Glu Gly Thr Pro Ser Tyr Pro Glu Ala Pro Gln Gln Pro Arg Tyr
        115                 120                 125

Val
```

```
<210> SEQ ID NO 15
<211> LENGTH: 4203
<212> TYPE: DNA
<213> ORGANISM: Lepeophtheirus salmonis

<400> SEQUENCE: 15
```

```
tattccaacg taacatgatc agaggatggg ctcaaagact ccaattgaac atggataaaa     60
tcaacaatca tggacatgga ttccattctg aagagcaatc catctttgga gattgtgata   120
ctctttacac tgttagtgat cataaaattg tgaaatctgt aagtcatact aaagattgca   180
aaaacagagt acgtgtcctc attgatgatt ggaggggcga acgctgtgac attgacccag   240
agcatccaga aagcagagaa atccaaatg gtctttactc tgcttccaac accatttatg    300
tcgtggacaa gaagggagat catttccacc ctaaggccat cattggatca tcctcagttg   360
ttgcacaatt ctatcaaatg gaaggagtct cctttattgc tcactctaat tcaacatcta   420
ttttgaaatc tgttgaagat atctcagaac ctatggttgt tgttggaatc ccagtcaagg   480
atctcaaata cgaatttgaa gataaagaat atcaatggaa ttctgacaga gacctcaagg   540
ctcgtgaaga acatttatcc actggtgaat ttttgagag tgacatgtcc actttgtcaa   600
aatatgttaa ggaaaagctc aacaagttcc atgcatcat gcaacatctt tcaaatgaca    660
aagatgccat tgcagaagct catgataatg gagtaaacag tatggtaccc ggtatgttgg   720
ctatggacta caatacattg aaggctatgt ctgaagaact tcactcagac aaatctgatg   780
aaggtgtatt caaatacaat cttttcaatg aacttttggg aagtttagga accagcgctt   840
ctgcactcct ggtccgtgac atgatcatgg aagacaaatt tgaaaacttc agggatgctg   900
tccgtgctct tactgccatt cctttccata ttcgtcaccc taacaagcaa cttttgagtg   960
```

```
aattcgaagc tttgtacaac tacgatggag atcaactcct caaagatgcc gtcccaattg   1020
ttcttggaca cttagcacga gttacctgcg aaagagccgg agtaatgcac tcccctgctt   1080
ctaaagaatg tttccactct gttgtcgatg gatacgccga taaacaatt gaaaaaatta   1140 tgggtgcatc tgaccacaaa gagcaaatta agcttcttgg aatgttgttc aatcttcgct   1200
atggaaacgt tgctgaaaaa ttaaagcctc ttatttatgg agaaactgag atcaaatgtg   1260
gacatctccg tactcttgct gttcaagctg ctgcttttgg agcaatcaac aacggaaagg   1320
gagctgaata tttattgccc attttttgcgg acagtgaaaa ctctcatgaa cttagattga   1380
cagctctctc atacttgatg gatgctcatc ccaccgcaac tcactttaac accatcgttg   1440
ctgtacttta cagagaaaaa gattatgaag ttatcaacta tgcttttaca ctcttggata   1500
aatatgcaac caatattaac ccctgcaaaa atcggtctc tgtattggcc aaatacttct   1560
tgaaatatct taagcaatac agtcattttg aaactgacta tggattggga gtgtccaaaa   1620
cttatagtcg tcaattccaa caatctaaat acgggtatgg aggtgaatac agctactggg   1680
tcattggatc tcatagttct accccttcctc tgagtgttgc aatgtgtatg gacacaacct   1740
tgtttggagg atataccgct aatggaatgt gtgtgcaatt aagaattgaa ggattgtcca   1800
aggctctcat ccgtaaattc aagacgatga gcccagatat ctggaaatct gaagatctca   1860
aaagtatctt aatgggagat atgaacatta aggaaagacc tgatcaacca atcaacgttg   1920
aggttctcct tttcgtcaag aactcagttg ttgcattcag acaatataac gaagattcaa   1980
ttaaggaagg tgggaacttg aaagaaattt tcgatcgatt gaaaggactt ggagacacct   2040
actccattaa tcaccaaaga gcaatgagat ttggaagcct cttgtaccaa caacccttgg   2100
aagtcggtgc tccagtctct tacttaaact cattcaccgg cgttttgat gttcaagcta   2160 caattaagaa gggaaatgcc agaggtctta tgttcagaga tgtcaaatat aacatgaact   2220
tttttggaca tggatctcgt atgatgatgg ttcaaaaccc acaatcaaag atgttttatt   2280
ccatttctca aaaccgcatt tatggctccc atttcccaag agaatttgtc attggagtta   2340
atccattgaa gaaagagttt aaattatcta ttcaacggcc ttcttatgag aatccactcg   2400
tacttatgat gcactcttta acaaaagttt acactggatc tcaaaatgtt aatgaaaagc   2460
aggatatttc agccaactgt cctgagtgca agtctgatac tcctgtatcg tatggtccag   2520
atgctgctaa aaccagagtc ttttaaacc atgattgcga taagactggc tcttatattc   2580
acggggaata ctttgactgt gaaatggaat ccaataggg aaaggtctta taccattgt   2640 ggagagccat gttaccttat aacaaaaacc ctaagacctt tggaaatggt attcgcatgg   2700
gtattcgtca atcagagct tattttgttt tcttcccaag agctgaaaaa tgtggagcaa   2760
tgcttcgctg gtcacaatca aggaaaatc cagttaaaga gcttgaaatt ctatgagat   2820 tcaatgctaa tcccaatggc gagcgtcttt tctttagagg acgtaaatgg gtagtcacaa   2880
ctattatcaa agccaaagga gaaccacaag atagggtata caaaattatt ttgggacatg   2940
aattcactcc tggatacatt gagaatcgtc tcaagtttag aatgcaaaga gctgcagttc   3000
ctggaattat gtctgattat tctatttgct tcaatatgga aaacaagtac ccagactttg   3060
gagaagagtt tatgacttat gacaagagca ctcaattaaa aatgactgga aaggcaaaac   3120
ttcaatatgg tgctgctgca gactgtgact ctactcctgg agaaatgaaa ttaagcttca   3180
aacatgaaac aactgaagaa gcaagagagg ctatgaaaca cacttggtac tatgaaaagt   3240
gtatggaaca gaagaaacag ccagaatggg caaacagagg tgataaactt ccattcacac   3300
aagcttgcca catgacaaca tgggatgcaa ctactgcacg taaatactca tggaagatga   3360
```

```
acttttgttaa gatgactgat cgcatgaatg ctattgtttc tcaattccaa agtatcatga      3420
aaactggtct tttaccttac tgggacattg atccagaaat tatcccagct acaagtgctg      3480
atccccacat gaatatcaaa gctacccttta aaaaccacga caagaatgtt gatatgtaca      3540
tggaaaccag tcagggaggt caacgtttca acgatattcc tcttagttta aattggcgcc      3600
caatgttgag aaaccttaag tttacatcca ccactagacg tctcatgcaa tacaaaatta      3660
tccatggatg tactaccaca attgaccatg tatatactct tgacaatgtc acatatcctt      3720
acacacctac ctcatgctgg acgttggctt ctggacactg ttccccacat ccaacttatg      3780 cagttttttgt caaaaagtct gcaggatctc atttagatgc taaaatttat ttgggcggtc      3840
acagcatcga attccaaaca agtggcccaa agaagattaa tgttctcatc aacggtgaag      3900
ctattgatgt aggagaggag gaacatgttc atgaacaaga cggacaagaa attttcaagg      3960
tcttaaaatg gggatcaagt tacagtgttt actccttctt gaaaatctgg gtagtctatg      4020
atggccatgc agtcagctta atccctgctc catctgttac gggtcaacat tgcggtttgt      4080
gtggaaactt caacagaaac caatatgatg aatttgaaag caaggatgct catcaattga      4140
agacatccga cgagcttgtt gaagattata atggaagtgt tgagaatttt atttcttttca      4200 tcg                                                                    4203

<210> SEQ ID NO 16
<211> LENGTH: 821
<212> TYPE: DNA
<213> ORGANISM: Lepeophtheirus salmonis

<400> SEQUENCE: 16
cttcttaaat cctgaaaagg tagtagtaga acttccacgg aaatggcgaa gaacaagaac       60
gtcggtaagc cgaggaacta caagttagcc tccggagtcg tccggttcgg caaatctaaa     120
atgtaccaca agaaggcaat ctataaattc ttgaagaaga caactcccaa aaaggttgag     180
gccagtaagc ccgccttcgt tgagaagaag gtcggaggtg ccaagaatgg gggtactcgt     240
atggttcgcg tcaagaagtt gaagaacgac ttccccacca tggaaagacg tgctcataga     300
atcgccaaga agcctgaaaa gctctctcgc agggtccgtc ctaccctcac ccctggaact     360
attgcagtta tccttgcagg tatccacaaa ggaaagagaa tcgtcattct caaggagctc     420
tccagtggaa tgcttctgat ttctggcccc ttcaagctta ataactgccc aattagaagg     480
attaatcaac gctatttgtt ggccacatca accaagctcg atgtttcatc cattaaaatg     540
cccgagaaca ttaatgatga ttacttccgt cgtttaagag ccgccaagaa gccagctggt     600
agtgtattcg aagtaaaaaa ggaagaatac aaaccttctg aacaacgtaa gaaggaccaa     660
gtcgaagttg ataagcagct cctcaatgtc atcatgaagc accccgaagc ctctctttttg     720 aaacaatact tgaagaagtc cttcggtctt agcaagggac aatatcctca taatatgaaa     780
ttttaattgt cgtcttgtta aataaaacta aaattcctcg c                         821

<210> SEQ ID NO 17
<211> LENGTH: 591
<212> TYPE: DNA
<213> ORGANISM: Lepeophtheirus salmonis

<400> SEQUENCE: 17
tcaatttgat tgatccagga agagaaacat gaagatcatt gccatctttg cacttttgtt       60
cattgccgtg tctggagagg atctggagtg ggagtcctgc aatcccgata acttgggaga     120
aggagacatt gccctctctc cttatcccct tccagtagtt agtggaacca gtctggattt     180
```

```
gaaagccctc tttgatcttc acaaggacct cgatggagat gtggatgttg aactcaagtt    240
ggtcaagaaa ggaattgtct ccattcccat cccctgcatt gaaagccctt caggcctgca    300
tttgggctct tgttcctaca aactggagga gattgtcagc aaatatgcgt atttcttgtg    360
tccagactat tttccagagg gccaaagctg ttctttccct ttgaaggcag gacaatatgg    420
aggtgagatc tctggtattg ttctacctga catcccacct tccatttcca acctcgccaa    480
gggaaccatt catggaactc tctctgtgac cagaaacggg gaagaagttt tctgtatcaa    540
tggagatttg aaaatgacaa attaatcctt gtttctgtat ccatatttga a             591
```

<210> SEQ ID NO 18
<211> LENGTH: 3718
<212> TYPE: DNA
<213> ORGANISM: Lepeophtheirus salmonis

<400> SEQUENCE: 18

```
ccattcaaga tgagagtcac agccctcctt tgcttatttg ttgccgctgt cagcggaagc     60
atatttgaag atggaaagca atatgtattt gattcagaga catctgttgt tgttggtacg    120
atggaccatg ctccacactc atctggattt gcttacaagc accatactac catgcaagtt    180
caaggagata acatcaaagt gaagctttct gacgttgaat tctcacaatt caatggaaaa    240
catgagaatg gagagttccc atttgaccac actaactttg ttgcaacaaa cagagacatt    300
cctgcatttg aagttcagtt ggactcccat ggattgtttt catccctcaa agttggtcct    360
aaactgacac tattccaacg taacatgatc agaggatggg ctcaaagact ccaattgaac    420
atggataaaa tcaacaatca tggacatgga ttccattctg aagagcaatc catctttgga    480
gattgtgata ctctttacac tgttagtgat cataaaattg tgaaatctgt aagtcatact    540
aaagattgca aaaacagagt acgtgtcctc attgatgatt ggaggggcga acgctgtgac    600
attgacccag agcatccaga aagcagagaa aatccaaatg gtctttactc tgcttccaac    660
accatttatg tcgtggacaa gaagggagat catttccacc ctaaggccat cattggatca    720
tcctcagttg ttgcacaatt ctatcaaatg gaaggagtct cctttattgc tcactctaat    780
tcaacatcta ttttgaaatc tgttgaagat atctcagaac ctatggttgt tgttggaatc    840
ccagtcaagg atctcaaata cgaatttgaa gataaagaat atcaatggaa ttctgacaga    900
gacctcaagg ctcgtgaaga acatttatcc actggtgaat tttttgagag tgacatgtcc    960
actttgtcaa aatatgttaa ggaaaagctc aacaagttcc atgacatcat gcaacatctt   1020
tcaaatgaca aagatgccat tgcagaagct catgataatg gagtaaacag tatggtaccc   1080
ggtatgttgg ctatggacta caatacattg aaggctatgt ctgaagaact tcactcagac   1140
aaatctgatg aaggtgtatt caaatacaat cttttcaatg aacttttggg aagtttagga   1200
accagcgctt ctgcactcct ggtccgtgac atgatcatgg aagacaaatt tgaaaacttc   1260
agggatgctg tccgtgctct tactgccatt cctttccata ttcgtcaccc tagcaagcaa   1320
cttttgagtg aattcgaagc tttgtacaac tacgatggag atcaactcct caaagatgcc   1380
gtcccaattg ttcttggaca cttagcacga gttacctgcg aaagagccgg agtaatgcac   1440
tcccctgctt ctaaagaatg tttccactct gttgtcgatg gatacgccga taaaacaatt   1500
gaaaaaatta tgggtgcatc tgaccacaaa gagcaaatta agcttcttgg aatgttgttc   1560
aatcttcgct atggaaacgt tgctgaaaaa ttaaagcctc ttatttatgg agaaactgag   1620
atcaaatgtg gacatctccg tactcttgct gttcaagctg ctgcttttgg agcaatcaac   1680
aacggaaagg gagctgaata tttattgccc atttttgcgg acagtgaaaa ctctcatgaa   1740
```

```
cttagattga cagctctctc atacttgatg gatgctcatc ccaccgcaac tcactttaac    1800
accatcgttg ctgtacttta cagagaaaaa gattatgaag ttatcaacta tgcttttaca    1860
ctcttggata aatatgcaac caatattaac ccctgcaaga aatcggtctc tgtattggcc    1920
aaatacttct tgaaatatct taagcaatac agtcattttg aaactgacta tggattggga    1980
gtgtccaaaa cttatagtcg tcaattccaa caatctaaat acgggtatgg aggtgaatac    2040
agctactggg tcattggatc tcatagttct acccttcctc tgagtgttgc aatgtgtatg    2100
gacacaacct tgtttggagg atataccgct aatggaatgt gtgtgcaatt aagaattgaa    2160
ggattgtcca aggctctcat ccgtaaattc aagacgatga gcccagatat ctggaaatct    2220
gaagatctca aaagtatctt aatgggagat atgaacatta aggaaagacc tgatcaacca    2280
atcaacgttg aggttctcct tttcgtcaag aactcagttg ttgcattcag acaatataac    2340
gaagattcaa ttaaggaagg tgggaacttg aaagaaattt tcgatcaatt gaaaggactt    2400
ggaggcacct actccattaa tcaccaagga gcaatgagat ttggaagcct cttgtaccaa    2460
caacccttgg aagtcggtgc tccagtctct tacttaaact cattcaccgg cgttttgat    2520 gttcaagcta caattaagaa gggaaatgcc agaggtctta tgttcagaga tgtcaaatat    2580
aacatgaact tttttggaca tggatctcgt atgatgatgg ttcaaaaccc acaatcaaag    2640
atgtttattt ccatttctca aaaccgcatt tatggctccc atttcccaag agaatttgtc    2700
attggagtta atccattgaa gaaagagttt aaattatcta ttcaacggcc ttcttatgag    2760
aatccactcg tacttatgat gcactcttta acaaaagttt acactggatc tcaaaatgtt    2820
aatgaaaagc aggatatttc agccaactgt cctgagtgca agtctgatac tcctgtatcg    2880
tatggtccag atgctgctaa aaccagagtc tttttaaacc atgattgcga taagactggc    2940
tcttatattc acggggaata ctttgactgt gaaatggaat ccaataggg aaaggtctta    3000 taccatttgt ggagagccat gttacctat aacaaaaacc ctaagacctt tggaaatggt     3060
attcgcatgg gtattcgtca aatcagagct tattttgttt tcttcccaag agctgaaaaa    3120
tgtggagcaa tgcttcgctg gtcacaatca aaggaaaatc cagttaaaga gcttgaaatt    3180
tctatgagat tcaatgctaa tcccaatggc gagcgtcttt tctttagagg acgtaaatgg    3240
gtagtcacaa ctattatcaa agccaaagga gaaccacaag atagggtata caaaattatt    3300
ttgggacatg aattcactcc tggatacatt gagaatcgtc tcaagtttag aatgcaaaga    3360
gctgcagttc ctggaattat gtctgattat tctattgct tcaatatgga aaacaagtac    3420
ccagactttg gagaagagtt tatgacttat gacaagagca ctcaattaaa aatgactgga    3480
aaggcaaaac ttcaatatgg tgctgctgca gactgtgact ctactcctgg agaaatgaaa    3540
ttaagcttca aacatgaaac aactgaagaa gcaagagagg ctatgaaaca cacttggtac    3600
tatgaaaagt gtatggaaca gaagaaacag ccagaatggg caaacagagg tgataaactt    3660
ccattcacac aagcttgcca catgacaaca tgggatgcaa ctactgctcc gtaaatac     3718
```

<210> SEQ ID NO 19
<211> LENGTH: 2428
<212> TYPE: DNA
<213> ORGANISM: Lepeophtheirus salmonis
<220> FEATURE:
<221> NAME/KEY: misc_feature
<222> LOCATION: (2077)
<223> OTHER INFORMATION: n = unknown nucleotide

<400> SEQUENCE: 19

```
ccaattctag ctagtcacta tgaactagtc aaaataattt atatactgtt tttatattga      60
```

```
ttttttattta tatattatta catccttgag gacttttgaa caaaggtgtt cgtagtaaac      120
ttttgagtca ttattacata gttgtcatac ctatttcaag gataataagg acgatcatca      180
tgaaaacatc tattattttc tcactgtatg ttctgccttc tatactgcac cttgctgtaa      240
gtgaagataa aactattata gctgaagacc tgacagctgt agagtcacgc tataaagtag      300
atgcaaaacc ctcaccttat gttcctccac aaccagcacc agattttgat tactttgcac      360
ccactgtatc tccttctttc tccccaatcg catctccctc tccttcttcc cctgttacat      420
cctactttac acccacaacc attcctccag tgactccctc gaccacaacg accactgtta      480
caacaacaac ccctgccaca tctacttaca gaaagttatt ctttccaacg tctttcaaac      540
catcttttct ttcttctcga aaaagttaa ccacaactac aacaacgccg gctacaacat       600
cctcaacaac aacaacaata accttcaccc caactacttc accccctcca tctgctaatg      660
aagttcgaac aacattaaac ccatccaaag tagcctcaaa aacaaagtca tatacccgcc      720
ctctttactc caaaaagaac ttcttacgca agaaaccctc tgtatattac aaagttaaga      780 aaatcccgt caagttaaga aaagttaaga aaattctgag acctgtgagt tactcaactc       840
ctcagactca tccgagcagc acgactgttt caaccacaag agactatcca agtaaatctc      900
ttgaaagttt aacgcaaact aagagtccag aaatagtatc ggcctttact ccggtctcag      960
tctcaaaaaa gtctattaaa tcattgaatg ctcgaaaatc catttatgca agtccatcta     1020
ccccatcttt tagatattca ccaacaacac cttcttcata tcaaagtctt aagccatttg     1080
agcccaaacc tattcataga ttcagatcta agccaggcta caagtctacc agatccaaac     1140
ctacttatgt ttcgtcaacg accacccacc cagcgtatgt atcatctact attagtccag     1200
cctatgcatc atctagtgtt agtccagcct atgcatcatc tagtgttagc ccagcctatg     1260
catccacaac agttaaacct gtctttgttt ctacgacagc aaatgaaata tactatacgc     1320
ccgaaccaaa aagggtacga agtcttccac ttacacgaga acaagcacat ctctattcat     1380
ctattcctta tgattcaaca actacatcaa ggcagcctcc agctcctgtt tcctacagta     1440
cacctaagcc ccactcgaaa caacatagcc aatatcgcga attgccattg actagagagc     1500
aaagtgaaaa cattgagttt agtactcccg taaaggctaa tacgaagcct tacaataata     1560
atatacaatt taatcctgta agacggattc cttctcatta tagaaatcat caagcgttga     1620
atgaaatacg tcgggaggaa agtatcctg cacaacccta ttccttcagc tatgatatca      1680
aagatgagac aagtggaacg gattttttcc gctctgaaga aagctcaggc cctgtgacga     1740
agggaagtta aaggtggct cttcctgatg gtcgtattca aattgttgaa tatattgcag      1800
atgaaaatgg ctataaggcc acagtttcct atgagggaga agctgttttc ccaaatccag     1860
atgattttga agaagaacca actcggagaa cttttagaca ctcaagaaaa gtcgatattg     1920
actctgtacc caataacaac tactcatttt tgcggaatag agtccgtggt gcagggacta     1980
cagaaaaagc tccttctcct caagacacaa ccattcgtcc agtcagtctt ccattaagac     2040
atcgattatc tcgtgccgaa gtctcaaaat cacttcntac gagtccgttt ccttatgctg     2100
tgagtagtac gtcaccagct ccattacctt ctagtcaagg cccacaacgt tttcgtgttc     2160
atcattcttc accaaatgtt gagggacgag tattacatca ctcaacacct ccagtcagct     2220
attcccaact cccccaaatc gcgacaactc aaaaacccag attccttcat aacgccaatt     2280
acgaagaagc attacgagac tatggaatta aggttgatta ttaataccgt tactttttg     2340 tgatccattt aatatgggtt ataaatatat ttattagtac tcattgttta tttattgtaa     2400
aagccgttta gttgttcaga tgaaaagtg                                       2428
```

<210> SEQ ID NO 20
<211> LENGTH: 1393
<212> TYPE: PRT
<213> ORGANISM: Lepeophtheirus salmonis

<400> SEQUENCE: 20

```
Phe Gln Arg Asn Met Ile Arg Gly Trp Ala Gln Arg Leu Gln Leu Asn
1               5                   10                  15

Met Asp Lys Ile Asn Asn His Gly His Gly Phe His Ser Glu Glu Gln
            20                  25                  30

Ser Ile Phe Gly Asp Cys Asp Thr Leu Tyr Thr Val Ser Asp His Lys
        35                  40                  45

Ile Val Lys Ser Val Ser His Thr Lys Asp Cys Lys Asn Arg Val His
    50                  55                  60

Val Leu Ile Asp Asp Trp Arg Gly Glu Arg Cys Asp Ile Asp Pro Glu
65                  70                  75                  80

His Pro Glu Ser Arg Glu Asn Pro Asn Gly Leu Tyr Ser Ala Ser Asn
                85                  90                  95

Thr Ile Tyr Val Val Asp Lys Lys Gly Asp His Phe His Pro Lys Ala
            100                 105                 110

Ile Ile Gly Ser Ser Ser Val Val Ala Gln Phe Tyr Gln Met Glu Gly
        115                 120                 125

Val Ser Phe Ile Ala His Ser Asn Ser Thr Ser Ile Leu Lys Ser Val
    130                 135                 140

Glu Asp Ile Ser Glu Pro Met Val Val Gly Ile Pro Val Lys Asp
145                 150                 155                 160

Leu Lys Tyr Glu Phe Glu Asp Lys Glu Tyr Gln Trp Asn Ser Asp Arg
                165                 170                 175

Asp Leu Lys Ala Arg Glu Glu His Leu Ser Thr Gly Glu Phe Phe Glu
            180                 185                 190

Ser Asp Met Ser Thr Leu Ser Lys Tyr Val Lys Glu Lys Leu Asn Lys
        195                 200                 205

Phe His Asp Ile Met Gln His Leu Ser Asn Asp Lys Asp Ala Ile Ala
    210                 215                 220

Glu Ala His Asp Asn Gly Val Asn Ser Met Val Pro Gly Met Leu Ala
225                 230                 235                 240

Met Asp Tyr Asn Thr Leu Lys Ala Met Ser Glu Glu Leu His Ser Asp
                245                 250                 255

Lys Ser Asp Glu Gly Val Phe Lys Tyr Asn Leu Phe Asn Glu Leu Leu
            260                 265                 270

Gly Ser Leu Gly Thr Ser Ala Ser Ala Leu Leu Val Arg Asp Met Ile
        275                 280                 285

Met Glu Asp Lys Phe Glu Asn Phe Arg Asp Ala Val Arg Ala Leu Thr
    290                 295                 300

Ala Ile Pro Phe His Ile Arg His Pro Ser Lys Gln Leu Leu Ser Glu
305                 310                 315                 320

Phe Glu Ala Leu Tyr Asn Tyr Asp Gly Asp Gln Leu Leu Lys Asp Ala
                325                 330                 335

Val Pro Ile Val Leu Gly His Leu Ala Arg Val Thr Cys Glu Arg Ala
            340                 345                 350

Gly Val Met His Ser Pro Ala Ser Lys Glu Cys Phe His Ser Val Val
        355                 360                 365

Asp Gly Tyr Ala Asp Lys Thr Ile Glu Lys Ile Met Gly Ala Ser Asp
    370                 375                 380
```

-continued

```
His Lys Glu Gln Ile Lys Leu Leu Gly Met Leu Phe Asn Leu Arg Tyr
385                 390                 395                 400

Gly Asn Val Ala Glu Lys Leu Lys Pro Leu Ile Tyr Gly Glu Thr Glu
                405                 410                 415

Ile Lys Cys Gly His Leu Arg Thr Leu Ala Val Gln Ala Ala Ala Phe
            420                 425                 430

Gly Thr Ile Asn Asn Gly Lys Gly Ala Glu Tyr Leu Leu Pro Ile Phe
        435                 440                 445

Ala Asp Ser Glu Asn Ser His Glu Leu Arg Leu Thr Ala Leu Ser Tyr
    450                 455                 460

Leu Met Asp Ala His Pro Thr Ala Thr His Phe Asn Thr Ile Val Ala
465                 470                 475                 480

Val Leu Tyr Arg Glu Lys Asp Tyr Glu Val Ile Asn Tyr Ala Phe Thr
                485                 490                 495

Leu Leu Asp Lys Tyr Ala Thr Asn Ile Asn Pro Cys Lys Lys Ser Val
            500                 505                 510

Ser Val Leu Ala Lys Tyr Phe Leu Lys Tyr Leu Lys Gln Tyr Ser His
        515                 520                 525

Phe Glu Thr Asp Tyr Gly Leu Gly Val Ser Lys Thr Tyr Ser Arg Gln
    530                 535                 540

Phe Gln Gln Ser Lys Tyr Gly Tyr Gly Glu Tyr Ser Tyr Trp Val
545                 550                 555                 560

Ile Gly Ser His Ser Ser Thr Leu Pro Leu Ser Val Ala Met Cys Met
                565                 570                 575

Asp Thr Thr Leu Phe Gly Gly Tyr Thr Ala Asn Gly Met Cys Val Gln
            580                 585                 590

Leu Arg Ile Glu Gly Leu Ser Lys Ala Leu Ile Arg Lys Phe Lys Thr
        595                 600                 605

Met Ser Pro Asp Ile Trp Lys Ser Glu Asp Leu Lys Ser Ile Leu Met
    610                 615                 620

Gly Asp Met Asn Ile Lys Glu Arg Pro Asp Gln Pro Ile Asn Val Glu
625                 630                 635                 640

Val Leu Leu Phe Val Lys Asn Ser Val Val Ala Phe Arg Gln Tyr Asn
                645                 650                 655

Glu Asp Ser Ile Lys Glu Gly Gly Asn Leu Lys Glu Ile Phe Asp Gln
            660                 665                 670

Leu Lys Gly Leu Gly Asp Thr Tyr Ser Ile Asn His Gln Arg Ala Met
        675                 680                 685

Arg Phe Gly Ser Leu Leu Tyr Gln Gln Pro Leu Glu Val Gly Ala Pro
    690                 695                 700

Val Ser Tyr Leu Asn Ser Phe Thr Gly Val Phe Asp Val Gln Ala Thr
705                 710                 715                 720

Ile Lys Lys Gly Asn Ala Arg Gly Leu Met Phe Arg Asp Val Lys Tyr
                725                 730                 735

Asn Met Asn Phe Phe Gly His Gly Ser Arg Met Met Val Gln Asn
            740                 745                 750

Pro Gln Ser Lys Met Phe Tyr Ser Ile Ser Gln Asn Arg Ile Tyr Gly
        755                 760                 765

Ser His Phe Pro Arg Glu Phe Val Ile Gly Val Asn Pro Leu Lys Lys
    770                 775                 780

Glu Phe Lys Leu Ser Ile Gln Arg Pro Ser Tyr Glu Asn Pro Leu Val
785                 790                 795                 800

Leu Met Met His Ser Leu Thr Lys Val Tyr Thr Gly Ser Gln Asn Val
```

-continued

```
                805                 810                 815
Asn Glu Lys Gln Asp Ile Ser Ala Asn Cys Pro Glu Cys Lys Ser Asp
            820                 825                 830

Thr Pro Val Ser Tyr Gly Pro Asp Ala Ala Lys Thr Arg Val Phe Leu
        835                 840                 845

Asn His Asp Cys Asp Lys Thr Gly Ser Tyr Ile His Gly Glu Tyr Phe
850                 855                 860

Asp Cys Glu Met Glu Ser Asn Arg Gly Lys Val Leu Tyr His Leu Trp
865                 870                 875                 880

Arg Ala Met Leu Pro Tyr Asn Lys Asn Pro Lys Thr Phe Gly Asn Gly
                885                 890                 895

Ile Arg Met Gly Ile Arg Gln Ile Arg Ala Tyr Phe Val Phe Phe Pro
            900                 905                 910

Arg Ala Glu Lys Cys Gly Ala Met Leu Arg Trp Ser Gln Ser Lys Glu
        915                 920                 925

Asn Pro Val Lys Glu Leu Glu Ile Ser Leu Arg Phe Asn Ala Asn Pro
    930                 935                 940

Asn Gly Glu Arg Leu Phe Phe Arg Gly Arg Lys Trp Val Val Thr Thr
945                 950                 955                 960

Ile Ile Lys Ala Lys Gly Glu Pro Gln Asp Arg Val Tyr Lys Ile Ile
                965                 970                 975

Leu Gly His Glu Phe Thr Pro Gly Tyr Ile Glu Asn Arg Leu Lys Phe
            980                 985                 990

Arg Met Gln Arg Ala Ala Val Pro Gly Ile Met Ser Asp Tyr Ser Ile
        995                 1000                1005

Cys Phe Asn Met Glu Asn Lys Tyr Pro Asp Phe Gly Glu Glu Phe
    1010                1015                1020

Met Thr Tyr Asp Lys Ser Thr Gln Leu Lys Met Thr Gly Lys Ala
    1025                1030                1035

Lys Leu Gln Tyr Gly Ala Ala Ala Asp Cys Asp Ser Thr Pro Gly
    1040                1045                1050

Glu Met Lys Leu Ser Phe Lys His Glu Thr Thr Glu Glu Ala Arg
    1055                1060                1065

Glu Ala Met Lys His Thr Trp Tyr Tyr Glu Lys Cys Met Glu Gln
    1070                1075                1080

Lys Lys Gln Pro Glu Trp Ala Asn Arg Gly Asp Lys Leu Pro Phe
    1085                1090                1095

Thr Gln Ala Cys His Met Thr Trp Asp Ala Thr Thr Ala Arg
    1100                1105                1110

Lys Tyr Ser Trp Lys Met Asn Phe Val Lys Met Thr Asp Arg Met
    1115                1120                1125

Asn Ala Ile Val Ser Gln Phe Gln Ser Ile Met Lys Thr Gly Leu
    1130                1135                1140

Leu Pro Tyr Trp Asp Ile Asp Pro Glu Ile Ile Pro Ala Thr Ser
    1145                1150                1155

Ala Asp Pro His Met Asn Ile Lys Ala Thr Leu Lys Asn His Asp
    1160                1165                1170

Lys Asn Val Asp Met Tyr Met Glu Thr Ser Gln Gly Gly Gln Arg
    1175                1180                1185

Phe Asn Asp Ile Pro Leu Ser Leu Asn Trp Arg Pro Met Leu Arg
    1190                1195                1200

Asn Leu Lys Phe Thr Ser Thr Arg Arg Leu Met Gln Tyr Lys
    1205                1210                1215
```

```
Ile Ile His Gly Cys Thr Thr Thr Ile Asp His Val Tyr Thr Leu
1220                1225                1230

Asp Asn Val Thr Tyr Pro Tyr Thr Pro Thr Ser Cys Trp Thr Leu
1235                1240                1245

Ala Ser Gly His Cys Ser Pro His Pro Thr Tyr Ala Val Phe Val
1250                1255                1260

Lys Lys Ser Ala Gly Ser His Leu Asp Ala Lys Ile Tyr Leu Gly
1265                1270                1275

Gly His Ser Ile Glu Phe Gln Thr Ser Gly Pro Lys Lys Ile Asn
1280                1285                1290

Val Leu Ile Asn Gly Glu Ala Ile Asp Val Gly Glu Glu His
1295                1300                1305

Val His Glu Gln Asp Gly Gln Glu Ile Phe Lys Val Leu Lys Trp
1310                1315                1320

Gly Ser Ser Tyr Ser Val Tyr Ser Phe Leu Lys Ile Trp Val Val
1325                1330                1335

Tyr Asp Gly His Ala Val Ser Leu Ile Pro Ala Pro Ser Val Thr
1340                1345                1350

Gly Gln His Cys Gly Leu Cys Gly Asn Phe Asn Arg Asn Gln Tyr
1355                1360                1365

Asp Glu Phe Glu Ser Lys Ala His Gln Leu Lys Thr Ser Asp
1370                1375                1380

Glu Leu Val Glu Asp Tyr Lys Trp Lys Cys
1385                1390

<210> SEQ ID NO 21
<211> LENGTH: 247
<212> TYPE: PRT
<213> ORGANISM: Lepeophtheirus salmonis

<400> SEQUENCE: 21

Met Ala Lys Asn Lys Asn Val Gly Lys Pro Arg Asn Tyr Lys Leu Ala
1               5                   10                  15

Ser Gly Val Val Arg Phe Gly Lys Ser Lys Met Tyr His Lys Ala
            20                  25                  30

Ile Tyr Lys Phe Leu Lys Lys Thr Thr Pro Lys Val Glu Ala Ser
        35                  40                  45

Lys Pro Ala Phe Val Glu Lys Lys Val Gly Gly Ala Lys Asn Gly Gly
50                  55                  60

Thr Arg Met Val Arg Val Lys Lys Leu Lys Asn Asp Phe Pro Thr Met
65                  70                  75                  80

Glu Arg Arg Ala His Arg Ile Ala Lys Lys Pro Glu Lys Leu Ser Arg
                85                  90                  95

Arg Val Arg Pro Thr Leu Thr Pro Gly Thr Ile Ala Val Ile Leu Ala
            100                 105                 110

Gly Ile His Lys Gly Lys Arg Ile Val Ile Leu Lys Glu Leu Ser Ser
        115                 120                 125

Gly Met Leu Leu Ile Ser Gly Pro Phe Lys Leu Asn Asn Cys Pro Ile
130                 135                 140

Arg Arg Ile Asn Gln Arg Tyr Leu Leu Ala Thr Ser Thr Lys Leu Asp
145                 150                 155                 160

Val Ser Ser Ile Lys Met Pro Glu Asn Ile Asn Asp Asp Tyr Phe Arg
                165                 170                 175

Arg Leu Arg Ala Ala Lys Lys Pro Ala Gly Ser Val Phe Glu Gly Lys
            180                 185                 190
```

-continued

```
Lys Glu Glu Tyr Lys Pro Ser Glu Gln Arg Lys Lys Asp Gln Val Glu
            195                 200                 205

Val Asp Lys Gln Leu Leu Asn Val Ile Met Lys His Pro Glu Ala Ser
    210                 215                 220

Leu Leu Lys Gln Tyr Leu Lys Ser Phe Gly Leu Ser Lys Gly Gln
225                 230                 235                 240

Tyr Pro His Asn Met Lys Phe
                245

<210> SEQ ID NO 22
<211> LENGTH: 178
<212> TYPE: PRT
<213> ORGANISM: Lepeophtheirus salmonis

<400> SEQUENCE: 22

Met Lys Ile Ile Ala Ile Phe Ala Leu Leu Phe Ile Ala Val Ser Gly
1               5                   10                  15

Glu Asp Leu Glu Trp Glu Ser Cys Asn Pro Asp Asn Leu Gly Glu Gly
            20                  25                  30

Asp Ile Ala Leu Ser Pro Tyr Pro Leu Pro Val Val Ser Gly Thr Ser
        35                  40                  45

Leu Asp Leu Lys Ala Leu Phe Asp Leu His Lys Asp Leu Asp Gly Asp
    50                  55                  60

Val Asp Val Glu Leu Lys Leu Val Lys Lys Gly Ile Val Ser Ile Pro
65                  70                  75                  80

Ile Pro Cys Ile Glu Ser Pro Ser Gly Leu His Leu Gly Ser Cys Ser
                85                  90                  95

Tyr Lys Leu Glu Glu Ile Val Ser Lys Tyr Ala Tyr Phe Leu Cys Pro
            100                 105                 110

Asp Tyr Phe Pro Glu Gly Gln Ser Cys Ser Phe Pro Leu Lys Ala Gly
        115                 120                 125

Gln Tyr Gly Gly Glu Ile Ser Gly Ile Val Leu Pro Asp Ile Pro Pro
    130                 135                 140

Ser Ile Ser Asn Leu Ala Lys Gly Thr Ile His Gly Thr Leu Ser Val
145                 150                 155                 160

Thr Arg Asn Gly Glu Glu Val Phe Cys Ile Asn Gly Asp Leu Lys Met
                165                 170                 175

Thr Asn

<210> SEQ ID NO 23
<211> LENGTH: 1234
<212> TYPE: PRT
<213> ORGANISM: Lepeophtheirus salmonis
<220> FEATURE:
<221> NAME/KEY: misc_feature
<222> LOCATION: (1018)
<223> OTHER INFORMATION: Xaa = unknown amino acid

<400> SEQUENCE: 23

Met Arg Val Thr Ala Leu Leu Cys Leu Phe Val Ala Ala Val Ser Gly
1               5                   10                  15

Ser Ile Phe Glu Asp Gly Lys Gln Tyr Val Phe Asp Ser Glu Thr Ser
            20                  25                  30

Val Val Val Gly Thr Met Asp His Ala Pro His Ser Ser Gly Phe Ala
        35                  40                  45

Tyr Lys His His Thr Thr Met Gln Val Gln Gly Asp Asn Ile Lys Val
    50                  55                  60

Lys Leu Ser Asp Val Glu Phe Ser Gln Phe Asn Gly Lys His Glu Asn
```

```
                65                  70                  75                  80
Gly Glu Phe Pro Phe Asp His Thr Asn Phe Val Ala Thr Asn Arg Asp
                    85                  90                  95

Ile Pro Ala Phe Glu Val Gln Leu Asp Ser His Gly Leu Phe Ser Ser
                100                 105                 110

Leu Lys Val Gly Pro Lys Leu Thr Leu Phe Gln Arg Asn Met Ile Arg
            115                 120                 125

Gly Trp Ala Gln Arg Leu Gln Leu Asn Met Asp Lys Ile Asn Asn His
        130                 135                 140

Gly His Gly Phe His Ser Glu Glu Ser Ile Phe Gly Asp Cys Asp
145                 150                 155                 160

Thr Leu Tyr Thr Val Ser Asp His Lys Ile Val Lys Ser Val Ser His
                165                 170                 175

Thr Lys Asp Cys Lys Asn Arg Val His Val Leu Ile Asp Asp Trp Arg
                180                 185                 190

Gly Glu Arg Cys Asp Ile Asp Pro Glu His Pro Glu Ser Arg Glu Asn
            195                 200                 205

Pro Asn Gly Leu Tyr Ser Ala Ser Asn Thr Ile Tyr Val Val Asp Lys
        210                 215                 220

Lys Gly Asp His Phe His Pro Lys Ala Ile Ile Gly Ser Ser Ser Val
225                 230                 235                 240

Val Ala Gln Phe Tyr Gln Met Glu Gly Val Ser Phe Ile Ala His Ser
                245                 250                 255

Asn Ser Thr Ser Ile Leu Lys Ser Val Glu Asp Ile Ser Glu Pro Met
                260                 265                 270

Val Val Val Gly Ile Pro Val Lys Asp Leu Lys Tyr Glu Phe Glu Asp
            275                 280                 285

Lys Glu Tyr Gln Trp Asn Ser Asp Arg Asp Leu Lys Ala Arg Glu Glu
        290                 295                 300

His Leu Ser Thr Gly Glu Phe Glu Ser Asp Met Ser Thr Leu Ser
305                 310                 315                 320

Lys Tyr Val Lys Glu Lys Leu Asn Lys Phe His Asp Ile Met Gln His
                325                 330                 335

Leu Ser Asn Asp Lys Asp Ala Ile Ala Glu Ala His Asp Asn Glu Val
                340                 345                 350

Asn Ser Met Val Pro Gly Met Leu Ala Met Asp Tyr Asn Thr Ser Lys
            355                 360                 365

Ala Met Ser Glu Glu Leu His Ser Asp Lys Ser Asp Glu Gly Val Phe
        370                 375                 380

Lys Tyr Asn Leu Phe Asn Glu Leu Leu Gly Ser Leu Gly Thr Ser Ala
385                 390                 395                 400

Ser Ala Leu Leu Val Arg Asp Met Ile Met Glu Asp Lys Phe Glu Asn
                405                 410                 415

Phe Arg Asp Ala Val Arg Ala Leu Thr Ala Ile Pro Phe His Ile Arg
                420                 425                 430

His Pro Ser Lys Gln Leu Leu Ser Glu Phe Glu Ala Leu Tyr Asn Tyr
            435                 440                 445

Asp Gly Asp Gln Leu Leu Lys Asp Ala Val Pro Ile Val Leu Gly His
        450                 455                 460

Leu Ala Arg Val Thr Cys Glu Arg Ala Gly Val Met His Ser Pro Ala
465                 470                 475                 480

Ser Lys Glu Cys Phe His Ser Val Val Asp Gly Tyr Ala Asp Lys Thr
                485                 490                 495
```

-continued

```
Ile Glu Lys Ile Met Gly Ala Ser Asp His Lys Glu Gln Ile Lys Leu
            500                 505                 510
Leu Gly Met Leu Phe Asn Leu Arg Tyr Gly Asn Val Ala Glu Lys Leu
        515                 520                 525
Lys Pro Leu Ile Tyr Gly Glu Thr Glu Ile Lys Cys Gly His Leu Arg
    530                 535                 540
Thr Leu Ala Val Gln Ala Ala Phe Gly Ala Ile Asn Asn Gly Lys
545                 550                 555                 560
Gly Ala Glu Tyr Leu Leu Pro Ile Phe Ala Asp Ser Glu Asn Ser His
                565                 570                 575
Glu Leu Arg Leu Thr Ala Leu Ser Tyr Leu Met Asp Ala His Pro Thr
            580                 585                 590
Ala Thr His Phe Asn Thr Ile Val Ala Val Leu Tyr Arg Glu Lys Asp
        595                 600                 605
Tyr Glu Val Ile Asn Tyr Ala Phe Thr Leu Leu Asp Lys Tyr Ala Thr
    610                 615                 620
Asn Ile Asn Pro Cys Lys Lys Ser Val Ser Val Leu Ala Lys Tyr Phe
625                 630                 635                 640
Leu Lys Tyr Leu Lys Gln Tyr Ser His Phe Glu Thr Asp Tyr Gly Leu
                645                 650                 655
Gly Val Ser Lys Thr Tyr Ser Arg Gln Phe Gln Gln Ser Lys Tyr Gly
            660                 665                 670
Tyr Gly Gly Glu Tyr Ser Tyr Trp Val Ile Gly Ser His Ser Ser Thr
        675                 680                 685
Leu Pro Leu Ser Val Ala Met Cys Met Asp Thr Thr Leu Phe Gly Gly
    690                 695                 700
Tyr Thr Ala Asn Gly Met Cys Val Gln Leu Arg Ile Glu Gly Leu Ser
705                 710                 715                 720
Lys Ala Leu Ile Arg Lys Phe Lys Thr Met Ser Pro Asp Ile Trp Lys
                725                 730                 735
Ser Glu Asp Leu Lys Ser Ile Leu Met Gly Asp Met Asn Ile Lys Glu
            740                 745                 750
Arg Pro Asp Gln Pro Ile Asn Val Glu Val Leu Leu Phe Val Lys Asn
        755                 760                 765
Ser Val Val Ala Phe Arg Gln Tyr Asn Glu Asp Ser Ile Lys Glu Gly
    770                 775                 780
Gly Asn Leu Lys Glu Ile Phe Asp Gln Leu Lys Gly Leu Gly Asp Thr
785                 790                 795                 800
Tyr Ser Ile Asn His Gln Arg Ala Met Arg Phe Gly Ser Leu Leu Tyr
                805                 810                 815
Gln Gln Pro Leu Glu Val Gly Ala Pro Val Ser Tyr Leu Asn Ser Phe
            820                 825                 830
Thr Gly Val Phe Asp Val Gln Ala Thr Ile Lys Lys Gly Asn Ala Arg
        835                 840                 845
Gly Leu Met Phe Arg Asp Val Lys Tyr Asn Met Asn Phe Phe Gly His
    850                 855                 860
Gly Ser Arg Met Met Met Val Gln Asn Pro Gln Ser Lys Met Phe Tyr
865                 870                 875                 880
Ser Ile Ser Gln Asn Arg Ile Tyr Gly Ser His Phe Pro Arg Glu Phe
                885                 890                 895
Val Ile Gly Val Asn Pro Leu Lys Lys Glu Phe Lys Leu Ser Ile Gln
            900                 905                 910
Arg Pro Ser Tyr Glu Asn Pro Leu Val Leu Met Met His Ser Leu Thr
        915                 920                 925
```

```
Lys Val Tyr Thr Gly Ser Gln Asn Val Asn Glu Lys Gln Asp Ile Ser
    930                 935                 940

Ala Asn Cys Pro Glu Cys Lys Ser Asp Thr Pro Val Ser Tyr Gly Pro
945                 950                 955                 960

Asp Ala Ala Lys Thr Arg Val Phe Leu Asn His Asp Cys Asp Lys Thr
                965                 970                 975

Gly Ser Tyr Ile His Gly Glu Tyr Phe Asp Cys Glu Met Glu Ser Asn
            980                 985                 990

Arg Gly Lys Val Leu Tyr His Leu Trp Arg Ala Met Leu Pro Tyr Asn
        995                 1000                1005

Lys Asn Pro Lys Thr Phe Gly Asn Gly Xaa Arg Met Gly Ile Arg
    1010                1015                1020

Gln Ile Arg Ala Tyr Phe Val Phe Phe Pro Arg Ala Glu Lys Cys
    1025                1030                1035

Gly Ala Met Leu Arg Trp Ser Gln Ser Lys Glu Asn Pro Val Lys
    1040                1045                1050

Glu Leu Glu Ile Ser Met Arg Phe Asn Ala Asn Pro Asn Gly Glu
    1055                1060                1065

Arg Leu Phe Phe Arg Gly Arg Lys Trp Val Val Thr Thr Ile Ile
    1070                1075                1080

Lys Ala Lys Gly Glu Pro Gln Asp Arg Val Tyr Lys Ile Ile Leu
    1085                1090                1095

Gly His Glu Phe Thr Pro Gly Tyr Ile Glu Asn Arg Leu Lys Phe
    1100                1105                1110

Arg Met Gln Arg Ala Ala Val Pro Gly Ile Met Ser Asp Tyr Ser
    1115                1120                1125

Ile Cys Phe Asn Met Glu Asn Lys Tyr Pro Asp Phe Gly Glu Glu
    1130                1135                1140

Phe Met Thr Tyr Asp Lys Ser Thr Gln Leu Lys Met Thr Gly Lys
    1145                1150                1155

Ala Lys Leu Gln Tyr Gly Ala Ala Ala Asp Cys Asp Ser Thr Pro
    1160                1165                1170

Gly Glu Met Lys Leu Ser Phe Lys His Glu Thr Thr Glu Glu Ala
    1175                1180                1185

Arg Glu Ala Met Lys His Thr Trp Tyr Tyr Glu Lys Cys Met Glu
    1190                1195                1200

Gln Lys Lys Gln Pro Glu Trp Ala Asn Arg Gly Asp Lys Leu Pro
    1205                1210                1215

Phe Thr Gln Ala Cys His Met Thr Thr Trp Asp Ala Thr Thr Ala
    1220                1225                1230

Pro

<210> SEQ ID NO 24
<211> LENGTH: 714
<212> TYPE: PRT
<213> ORGANISM: Lepeophtheirus salmonis

<400> SEQUENCE: 24

Met Lys Thr Ser Ile Ile Phe Ser Leu Tyr Val Leu Pro Ser Ile Leu
1               5                   10                  15

His Leu Ala Val Ser Glu Asp Lys Thr Ile Ile Ala Glu Asp Leu Thr
                20                  25                  30

Ala Val Glu Ser Arg Tyr Lys Val Asp Ala Lys Pro Ser Pro Tyr Val
            35                  40                  45
```

```
Pro Pro Gln Pro Ala Pro Asp Phe Asp Tyr Phe Ala Pro Thr Val Ser
    50              55                  60

Pro Ser Phe Ser Pro Ile Ala Ser Pro Ser Pro Ser Ser Pro Val Thr
 65              70                  75                  80

Ser Tyr Phe Thr Pro Thr Thr Ile Pro Pro Val Thr Pro Ser Thr Thr
                 85                  90                  95

Thr Thr Thr Val Thr Thr Thr Thr Pro Ala Thr Ser Thr Tyr Arg Lys
            100                 105                 110

Leu Phe Phe Pro Thr Ser Phe Lys Pro Ser Phe Leu Ser Ser Arg Lys
        115                 120                 125

Lys Leu Thr Thr Thr Thr Thr Thr Pro Ala Thr Thr Ser Ser Thr Thr
    130                 135                 140

Thr Thr Ile Thr Phe Thr Pro Thr Thr Ser Pro Pro Pro Ser Ala Asn
145             150                 155                     160

Glu Val Arg Thr Thr Leu Asn Pro Ser Lys Val Ala Ser Lys Thr Lys
                165                 170                 175

Ser Tyr Thr Arg Pro Leu Tyr Ser Lys Lys Asn Phe Leu Arg Lys Lys
                180                 185                 190

Pro Ser Val Tyr Lys Val Lys Lys Asn Pro Val Lys Leu Arg Lys
        195                 200                 205

Val Lys Lys Ile Leu Arg Pro Val Ser Tyr Ser Thr Pro Gln Thr His
    210                 215                 220

Pro Ser Ser Thr Thr Val Ser Thr Thr Arg Asp Tyr Pro Ser Lys Ser
225             230                 235                     240

Leu Glu Ser Leu Thr Gln Thr Lys Ser Pro Glu Ile Val Ser Ala Phe
                245                 250                 255

Thr Pro Val Ser Val Ser Lys Lys Ser Ile Lys Ser Leu Asn Ala Arg
            260                 265                 270

Lys Ser Ser Tyr Ala Ser Pro Ser Thr Pro Ser Phe Arg Tyr Ser Pro
    275                 280                 285

Thr Thr Pro Ser Ser Tyr Gln Ser Leu Lys Pro Phe Glu Pro Lys Pro
    290                 295                 300

Ile His Arg Phe Arg Ser Lys Pro Gly Tyr Lys Ser Thr Arg Ser Lys
305             310                 315                     320

Pro Thr Tyr Val Ser Ser Thr Thr Thr His Pro Ala Tyr Val Ser Ser
                325                 330                 335

Thr Ile Ser Pro Ala Tyr Ala Ser Ser Val Ser Pro Ala Tyr Ala
            340                 345                 350

Ser Ser Ser Val Ser Pro Ala Tyr Ala Ser Thr Thr Val Lys Pro Val
        355                 360                 365

Phe Val Ser Thr Thr Ala Asn Glu Ile Tyr Tyr Thr Pro Glu Pro Lys
    370                 375                 380

Arg Val Arg Ser Leu Pro Leu Thr Arg Glu Gln Ala His Leu Tyr Ser
385             390                 395                     400

Ser Ile Pro Tyr Asp Ser Thr Thr Thr Ser Arg Gln Pro Pro Ala Pro
                405                 410                 415

Val Ser Tyr Ser Thr Pro Lys Pro His Ser Lys Gln His Ser Gln Tyr
            420                 425                 430

Arg Glu Leu Pro Leu Thr Arg Glu Gln Ser Glu Asn Ile Glu Phe Ser
        435                 440                 445

Thr Pro Val Lys Ala Asn Thr Lys Pro Tyr Asn Asn Ile Gln Phe
    450                 455                 460

Asn Pro Val Arg Arg Ile Pro Ser His Tyr Arg Asn His Gln Ala Leu
465             470                 475                     480
```

```
Asn Glu Ile Arg Arg Glu Glu Lys Tyr Pro Ala Gln Pro Tyr Ser Phe
                485                 490                 495

Ser Tyr Asp Ile Lys Asp Glu Thr Ser Gly Thr Asp Phe Phe Arg Ser
            500                 505                 510

Glu Glu Ser Ser Gly Pro Val Thr Lys Gly Ser Tyr Lys Val Ala Leu
        515                 520                 525

Pro Asp Gly Arg Ile Gln Ile Val Glu Tyr Ile Ala Asp Glu Asn Gly
    530                 535                 540

Tyr Lys Ala Thr Val Ser Tyr Glu Gly Glu Ala Val Phe Pro Asn Pro
545                 550                 555                 560

Asp Asp Phe Glu Glu Glu Pro Thr Arg Arg Thr Phe Arg His Ser Arg
                565                 570                 575

Lys Val Asp Ile Asp Ser Val Pro Asn Asn Tyr Ser Phe Leu Arg
            580                 585                 590

Asn Arg Val Arg Gly Ala Gly Thr Thr Glu Lys Ala Pro Ser Pro Gln
        595                 600                 605

Asp Thr Thr Ile Arg Pro Val Ser Leu Pro Leu Arg His Arg Leu Ser
    610                 615                 620

Arg Thr Glu Val Ser Lys Ser Leu Pro Thr Ser Pro Phe Pro Tyr Ala
625                 630                 635                 640

Val Ser Ser Thr Ser Pro Ala Pro Leu Pro Ser Ser Gln Gly Pro Gln
                645                 650                 655

Arg Phe Arg Val His His Ser Ser Pro Asn Val Glu Gly Arg Val Leu
            660                 665                 670

His His Ser Thr Pro Pro Val Ser Tyr Ser Gln Leu Pro Gln Ile Ala
        675                 680                 685

Thr Thr Gln Lys Pro Arg Phe Leu His Asn Ala Asn Tyr Glu Glu Ala
    690                 695                 700

Leu Arg Asp Tyr Gly Ile Lys Val Asp Tyr
705                 710

<210> SEQ ID NO 25
<211> LENGTH: 9
<212> TYPE: PRT
<213> ORGANISM: Lepeophtheirus salmonis

<400> SEQUENCE: 25

Phe Ile Asp Trp Ile Ala Glu His Gln
1               5

<210> SEQ ID NO 26
<211> LENGTH: 11
<212> TYPE: PRT
<213> ORGANISM: Lepeophtheirus salmonis

<400> SEQUENCE: 26

Ile Ala Val Ser Asp Ile Thr Tyr His Glu Lys
1               5                   10

<210> SEQ ID NO 27
<211> LENGTH: 27
<212> TYPE: PRT
<213> ORGANISM: Lepeophtheirus salmonis
```

```
<400> SEQUENCE: 27

Asp Gln Glu Phe Ile Gly Asp Val Val Ser Gly Trp Gly Thr Ile
1               5                   10                  15

Ser Ser Ser Gly Pro Pro Ser Pro Val Leu Lys
            20                  25

<210> SEQ ID NO 28
<211> LENGTH: 9
<212> TYPE: PRT
<213> ORGANISM: Lepeophtheirus salmonis

<400> SEQUENCE: 28

Asn Gln Tyr Asp Glu Phe Glu Ser Lys
1               5

<210> SEQ ID NO 29
<211> LENGTH: 12
<212> TYPE: PRT
<213> ORGANISM: Lepeophtheirus salmonis

<400> SEQUENCE: 29

Leu Ser Phe Glu His Glu Thr Thr Glu Glu Ala Arg
1               5                   10

<210> SEQ ID NO 30
<211> LENGTH: 15
<212> TYPE: PRT
<213> ORGANISM: Lepeophtheirus salmonis

<400> SEQUENCE: 30

Ile Ile Leu Gly His Glu Phe Thr Pro Gly Tyr Ile Glu Asn Arg
1               5                   10                  15

<210> SEQ ID NO 31
<211> LENGTH: 11
<212> TYPE: PRT
<213> ORGANISM: Lepeophtheirus salmonis

<400> SEQUENCE: 31

Ile Val Ile Leu Lys Glu Leu Ser Ser Gly Met
1               5                   10

<210> SEQ ID NO 32
<211> LENGTH: 25
<212> TYPE: PRT
<213> ORGANISM: Lepeophtheirus salmonis

<400> SEQUENCE: 32

Ala Gly Gln Tyr Gly Gly Glu Ile Ser Gly Ile Val Leu Pro Asn Ile
1               5                   10                  15

Pro Pro Ser Ile Ser Asn Leu Ala Lys
            20                  25

<210> SEQ ID NO 33
<211> LENGTH: 15
<212> TYPE: PRT
<213> ORGANISM: measles

<400> SEQUENCE: 33

Leu Ser Glu Ile Lys Gly Val Ile Val His Arg Leu Glu Gly Val
1               5                   10                  15
```

```
<210> SEQ ID NO 34
<211> LENGTH: 15
<212> TYPE: PRT
<213> ORGANISM: tetanus toxin

<400> SEQUENCE: 34

Gln Tyr Ile Lys Ala Asn Ser Lys Phe Ile Gly Ile Thr Glu Leu
1               5                   10                  15
```

RECOMBINANT VACCINES AGAINST CALIGID COPEPODS (SEA LICE) AND ANTIGEN SEQUENCES THEREOF

This application is a national phase entry based on International Patent Application PCT/CA2005/001178, which is entitled to the benefit of and claims priority to U.S. provisional patent application Ser. No. 60/591,626, filed Jul. 28, 2004, which is herein incorporated by reference.

FIELD OF THE INVENTION

The present invention relates generally to salmon vaccines. More particularly, the present invention relates to vaccines against parasitic caligid copepods (sea lice) and antigen sequences thereof.

BACKGROUND OF THE INVENTION

A number of closely related species of parasitic copepods in the family Caligidae (caligid copepods) infect and cause disease in cultured fish. Collectively, these species are referred to as sea lice. There are three major genera of sea lice: *Pseudocaligus, Caligus* and *Lepeophtheirus*. With respect to salmonid production throughout the northern hemisphere, one species, the salmon louse (*Lepeophtheirus salmonis*), is responsible for most disease outbreaks on farmed salmonids. This parasite is responsible for indirect and direct losses in aquaculture in excess of US $100 million annually (Johnson, S. C., et al., Zool Studies 43: 8-19, 2004). All developmental stages of sea lice, which are attached to the host, feed on host mucus, skin and blood. The attachment and feeding activities of sea lice result in lesions that vary in their nature and severity depending upon: the species of sea lice, their abundance, the developmental stages present and the species of the host (Johnson, S. C. et al., "Interactions between sea lice and their hosts". In: *Host-Parasite Interactions*. Editors: G. Wiegertjes and G. Flik, Garland Science/Bios Science Publications, 2004, pp. 131-160). In the southern hemisphere, *Caligus rogercresseyi*, is the primary caligid affecting the salmon farming industry in Chile (González, L. and Carvajal, J. Aquaculture 220: 101-117, 2003).

Caligid copepods have direct life cycles consisting of two free-living planktonic nauplius stages, one free-swimming infectious copepodid stage, four to six attached chalimus stages, one or two preadult stages, and one adult stage (Kabata, Z., Book 1: Crustacea as enemies of fishes. In: *Diseases of Fishes.*, Editors: Snieszko, S. F. and Axelrod, H. R.; New York, T.F.H. Publications, 1970, p. 171). Each of these developmental stages is separated by a moult. Once the adult stage is reached caligid copepods do not undergo additional moults. In the case of *L. salmonis*, eggs hatch into the free-swimming first nauplius stage, which is followed by a second nauplius stage, and then the infectious copepodid stage. Once the copepodid locates a suitable host fish it continues its development through four chalimus stages, first and second preadult stages, and then a final adult stage (Schram, T. A. "Supplemental descriptions of the developmental stages of *Lepeophtheirus salmonis* (Krøyer, 1837) (Copepoda: Caligidae)". In: *Pathogens of Wild and Farmed Fish*: Sea Lice. Editors: Boxshall, G. A. and Defaye, D., 1993, pp. 30-50). The moults are characterized by gradual changes as the animal grows and undertakes physical modifications that enable it to live as a free-roaming parasite, feeding and breeding on the surface of the fish.

Caligid copepods (sea lice) feed on the mucus, skin and blood of their hosts leading to lesions that vary in severity based on the developmental stage(s) of the copepods present, the number of copepods present, their site(s) of attachment and the species of host. In situations of severe disease, such as is seen in Atlantic salmon (*Salmo salar*) when infected by high numbers of *L. salmonis*, extensive areas of skin erosion and hemorrhaging on the head and back, and a distinct area of erosion and sub-epidermal hemorrhage in the perianal region can be seen (Grimnes, A. et al. J Fish Biol 48: 1179-1194, 1996). Sea lice can cause physiological changes in their hosts including the development of a stress response, reduced immune function, osmoregulatory failure and death if untreated (Johnson et al., supra).

There are several management strategies that have been used for reducing the intensity of caligid copepod (sea lice) infestations. These include: fallowing of sites prior to restocking, year class separation and selection of farm sites to avoid areas where there are high densities of wild hosts or other environmental conditions suitable for sea lice establishment (Pike, A. W. et al. Adv Parasitol 44: 233-337, 1999). Although the use of these strategies can in some cases lessen sea lice infection rates, their use individually or in combination has not been effective in eliminating infection.

A variety of chemicals and drugs have been used to control sea lice. These chemicals were designed for the control of terrestrial pests and parasites of plants and domestic animals. They include compounds such as hydrogen peroxide, organophosphates (e.g., dichlorvos and azamethiphos), ivermectin (and related compounds such as emamectin benzoate), insect molting regulators and pyrethrins (MacKinnon, B. M., World Aquaculture 28: 5-10, 1997; Stone J., et al., J Fish Dis 22: 261-270, 1999). Sea lice treatments can be classified into those that are administered by bath (e.g. organophosphates, pyrethrins) and those administered orally (e.g. ivermectin). Bath treatments for sea lice control are difficult, expensive to apply and can have significant effects of fish growth following treatments (MacKinnon, supra). Chemicals used in bath treatments are not necessarily effective against all of the stages of sea lice found on fish. At present the use of oral treatments such as SLICE® (emamectin benzoate) is predominant in the salmonid industry. Unlike chemicals administered as bath treatments SLICE® does provide short-term protection against re-infection. This treatment although easier to apply than bath treatments is still expensive and, like bath treatments, requires a withdrawal period before animals can be slaughtered for human consumption (Stone, supra). As seen in terrestrial pest and parasites there is evidence for the development of resistance in *L. salmonis* to some of these treatments, especially in frequently-treated populations (Denholm, I., Pest Manag Sci 58: 528-536, 2002). To reduce the costs associated with sea lice treatments and to eliminate environmental risks associated with these treatments new methods of sea lice control such as vaccines are needed.

A characteristic feature of attachment and feeding sites of caligid copepods on many of their hosts is a lack of a host immune response (Johnson et al., supra; Jones, M. W., et al., J Fish Dis 13: 303-310, 1990; Jónsdóttir, H., et al., J Fish Dis 15: 521-527, 1992). This lack of an immune response is similar to that reported for other arthropod parasites such as ticks on terrestrial animals. In those instances suppression of the host immune response is due to the production of immunomodulatory substances by the parasite (Wikel, S. K., et al., "Arthropod modulation of host immune responses". In The *Immunology of Host-Ectoparasitic Arthropod Relationships*. Editors: Wikel, S. K., CAB Int., 1996, pp. 107-130). These substances are being investigated for use as vaccine antigens to control these parasites. Sea lice, such as *L. salmonis*, like other arthropod ectoparasites, produce biologically active substances at the site of attachment and feeding that limits the host immune response. As these substances have potential for use in a vaccine against sea lice we have identified a number of these substances from *L. salmonis* and have examined their effects of host immune function in vitro.

Potential antigens have been identified using a combination of molecular biological, proteomic, biochemical and immunological techniques. For example, an increase in protease activity has been observed in the mucus of *L. salmonis* infected Atlantic salmon, compared to non-infected fish (Ross, N. W., et al., Dis Aquat Org 41: 43-51, 2000; Fast, M. D., et al., Dis Aquat Org 52: 57-68, 2002). This increased activity is primarily due to the appearance of a series of low molecular weight (18-24 kDa) proteins, that are produced by *L. salmonis* and were identified as trypsins based on activity, inhibition studies and size. Trypsin activity was identified in infected salmon mucus using aminobenzamidine affinity adsorption and protease zymography (Firth, K. J., et al., J Parasitol 86: 1199-1205, 2000). Several genes encoding for trypsin have been characterized from *L. salmonis* and the site of trypsin expression determined (Johnson, S. C., et al., Parasitol Res 88: 789-796, 2002; Kvamme, B. O., et al., Int. J. Parasitol. 34, 823-832, 2004; Kvamme, B. O. et al., Gene 352:63-72, 2005).

Several cDNA libraries have been developed from the copepodid, preadult and adult stages of *L. salmonis*. An expressed sequence tag (EST) study of the preadult library resulted in the identification of a number of genes encoding trypsin and related proteases (including chymotrypsin and others in the peptidase S1 family), heat shock proteins, cuticle proteins and metabolic enzymes. Some of these genes as described herein have utility as antigens in a sea lice vaccine.

Trypsin-like activity is secreted by *L. salmonis* onto the salmon skin and is believed to be used by the sea lice to feed on the salmon mucus, skin and blood and to protect the sea lice from the salmon immune response (Firth, et al. supra). Trypsin was discovered in the secretion products (SPs) of sea lice, following stimulation with dopamine, by amino acid sequencing using mass-spectrometry. Table 1 shows the peptide sequences of *L. salmonis* secreted trypsin. Protection against sea lice trypsin may reduce the feeding of the lice and reduce the suppression of the immune response.

TABLE 1

Summary of *L. salmonis* secreted trypsin identified from LC/MS/MS

| Sea Lice protein matches | Assoc. Fraction (pool#-fraction#) | Parent Ion (m/z) | Mr (Da) | Error (ppm)[a] | Score[b] | Peptide sequence (Start-end)[c] |
|---|---|---|---|---|---|---|
| Sea Lice Trypsin (types 1-4) | 1-2 | 579.80 | 1157.77 | 27 | 46 | [215]FIDWIAEHQ[223] (SEQ ID NO: 25) |
| | 1-1 | 638.35 | 1274.69 | 38 | 72 | [71]IAVSDITYHEK[81] (SEQ ID NO: 26) |
| | 3-6 | 920.18 | 1840.28 | 13 | 25 | [115]DQEFIGDVVVSGWGTI SSSGPPSPVLK[141] (SEQ ID NO: 27) |
| SL-0903 vitellogenin-like | 1-1 | 580.28 | 1158.48 | 46 | 27 | NQYDEFESK (SEQ ID NO: 28) |
| SL-1469 SEP protein 3 | 1-1 | 724.85 | 1447.66 | 17 | 24 | LSFEHETTEEAR (SEQ ID NO: 29) |
| | 1-2 | 879.98 | 1757.91 | 29 | 72 | IILGHEFTPGYIENR (SEQ ID NO: 30) |
| SL-0547 SEP protein 1 | 1-1 | 604.31 | 1204.67 | 19 | 25 | IVILKELSSGM (SEQ ID NO: 31) + M oxidation[d] |
| SL-0858 SEP Protein 2 | 1-2 | 1248.71 | 2495.33 | 65 | 35 | AGQYGGEISGIVLPNIP PSISNLAK (SEQ ID NO: 32) |

[a]Difference (in parts-per-million) between measured mass and mass predicted from the DNA sequence.
[b]Score from MASCOT™ search, scores above 21 indicate identity or extensive homology (p < 0.05)
[c]Cyanogen bromide/tryptic peptide sequence predicted from the DNA sequence.
[d]+M oxidation means that the MASCOT match was for a peptide containing an oxidized methionine residue.

Vitellogenin-like protein was discovered in the secretion products (SPs) of sea lice following stimulation with dopamine. Vitellogenin has previously been reported as an effective antigen in a tick vaccine (Tellam, R. I., et al., Vet Parasitol 103: 141-156, 2002). Inclusion of vitellogenin in a sea lice vaccine may interfere with the fecundity of sea lice and reduce the number of offspring and hence reduce future numbers of sea lice. In addition, vitellogenin-like proteins have been implicated in the synthesis of melanin in invertebrates (Lee, K. M. et al., Eur J Biochem 267:3695-3703, 2000). Melanin is an important defence molecule of invertebrates.

Mussel adhesion-like genes express proteins similar to those found in the mussel byssus threads that mussels use to attach themselves to solid surfaces. How these genes relate to sea lice infestation is not currently understood, but they may be involved in the production of frontal filaments. The frontal filament is used by chalimus stages to physically attach themselves to the host (Gonzalez-Alanis, P., et al., J Parasitol 87: 561-574, 2001).

BCS-1 genes are expressed by barnacles when they switch from a planktonic form to an attached form (Okazaki, Y., et al., Gene 250 (1-2): 127-135, 2000). There is currently evidence to suggest that these are cuticle-binding proteins. Disruption of these proteins by antibodies may interfere with moulting, integrity of the sea lice cuticle and normal growth of the lice.

Secretory proteins produced by the sea lice may act as immunomodulatory agents or assist in the feeding activities on the host (Fast, M. D., et al., Exp Parasitol. 107:5-13, 2004;

Fast, M. D., et al., J Parasitol 89: 7-13, 2003). Neutralization of these activities by host-derived antibodies may impair sea lice growth and survival on salmon.

Vaccines are generally safer than chemical treatments, both to the fish and to the environment. However, no commercial vaccines against sea lice have been developed to date. Vaccine development has been hindered by a lack of knowledge of the host-pathogen interactions between sea lice and their hosts. There appears to be very limited antibody response in naturally infected hosts. Experimental vaccines, particularly through whole-animal extracts, have been produced against *L. salmonis*. Investigations in the development of sea lice vaccines have targeted immunogenic proteins from sea lice and, in particular, targeting gut antigens. These vaccines, based on whole animal extracts, have not been shown to be protective though their administration did result in minor changes in *L. salmonis* fecundity (Grayson T. H., et al., J Fish Biol 47: 85-94, 1995). This particular study, however, was a one-time trial and no further results have been reported from this group. Liposome-based fish vaccines in certain species of fin-fish have also been explored (Keough, PCT Application WO 03/101482) but not in combination with sea lice antigens.

A more recent discussion of possible vaccine targets in the gut was put forth by Raynard et al.; however, their studies have been met with limited success (Raynard, R. S., et al., Pest Manag Sci 58: 569-575, 2002).

Promiscuous T-Cell Epitopes

Promiscuous T-cell epitopes (or "PTC epitopes") are highly immunogenic peptides that can be characterized in part by their capacity to bind several isotypic and allotypic forms of human MHC class II molecules. By helping to bypass MHC restriction, they can induce T-cell and antibody responses in members of a genetically diverse population expressing diverse MHC haplotypes. The PTC epitopes can therefore be combined with antigens that, by themselves, are poorly immunogenic, to generate potent peptide immunogens. In the present invention, these epitopes are incorporated into the composition to enhance the immunogenicity of the antigen, and the composition overall, in a broad range of species.

Promiscuous T-cell epitopes can be derived from naturally occurring immunogens of viral and bacterial origin. Naturally occurring PTC epitopes can also be conservatively modified by single- or multiple-amino acid additions, deletions or substitutions (e.g. within classes of charged, hydrophilic/hydrophobic, steric amino acids) to obtain candidate sequences that can be screened for their ability to enhance immunogenicity.

Non-naturally occurring PTC epitopes can be artificially synthesized to obtain sequences that have comparable or better immunogenicity. Artificial PTC epitopes can range in size from about 15 to about 50 amino acid residues in length and can have structural features such as amphipathic helices, which are alpha-helical structures with hydrophobic amino acid residues dominating one face of the helix and charged or polar residues dominating the surrounding faces. The PTC epitopes may also contain additional primary amino acid patterns, such as a Gly or a charged residue followed by two to three hydrophobic residues, followed in turn by a charged or polar residue (a Rothbard sequence). In addition, PTC epitopes often obey the 1, 4, 5, 8 rule, where a positively charged residue is followed by hydrophobic residues at the fourth, fifth, and eighth positions after the charged residue.

These features may be incorporated into the designs of artificial PTC epitopes. Variable positions and preferred amino acids are available for MHC-binding motifs (Meister et al., Vaccine, 1995; 13:581-591). For example, the degenerate PTC epitope described in WO 95/11998 as SSAL1TH1 has the degenerate sequence (Asp/Glu)-(Leu/Ile/Val/Phe)-Ser-(Asp/Gly)-(Leu/Ile/Val/Phe)-(Lys/Arg)-Gly-(Leu/Ile/Val/Phe)-(Leu/Ile/Val/Phe)-(Leu/Ile/Val/Phe)-His-(Lys/Arg)-Leu/Ile/Val/Phe)-(Asp/Glu)-Gly-(Leu/Ile/Val/Phe)-.

Specific Examples of PTC Epitopes

Particularly useful promiscuous T-cell epitopes are measles virus protein F LSEIKGVIVHRLEGV (SEQ ID NO: 33); or tetanus sequence QYIKANSKFIGITEL (SEQ ID NO: 34).

Examples of particularly useful promiscuous T-cell epitopes are listed in Table 2:

TABLE 2

Examples of Promiscuous T-cell Epitopes

| description | amino acid sequence | SEQ ID NO: |
|---|---|---|
| measles 289-302 | LSEIKGVIVHRLEGV | 33 |
| tetanus toxin 830-844 | QYIKANSKFIGITEL | 34 |

Because of a lack of understanding of the mechanisms and pathology surrounding sea lice infestation of salmon, identification of suitable targets to treat the disease has not been successful. This has hampered the progress of vaccine research and as such, despite the promise and success of vaccine-based therapies in other areas of infection, a suitable sea lice vaccine has yet to be developed. Consequently, there is a need to provide effective suitable molecular targets (antigens) and a vaccine against sea lice infection.

SUMMARY OF THE INVENTION

It is an object of the present invention to obviate or mitigate at least one disadvantage of previous treatments against sea lice infection in fish.

In a first aspect, the present invention provides a vaccine against caligid copepod infection in fish, the vaccine comprising an immunologically effective amount of antigen. Particularly, the caligid copepod is *Lepeophtheirus salmonis*, although any copepod infection may be treated. In one embodiment, the vaccine comprises a nucleotide or peptide fragment of *L. salmonis* trypsin and a pharmaceutically-acceptable adjuvant, diluent or carrier.

In another aspect of the present invention there are provided DNA and amino acid sequences encoding antigens for use in the preparation of vaccine formulations for the treatment of caligid copepod infection in fish. Embodiments of these sequences include secretory products (SEPs) 1, 2 and 3, vitellogenin-like protein, melanization-related protein, adhesion protein 1 and 2, and cuticle binding protein 1.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 1 shows the a) nucleic acid sequence and b) amino acid sequence of vitellogenin-like protein (SEQ ID NO: 1, 2).

FIG. 2 shows the a) nucleic acid sequence and b) amino acid sequence of SEP protein 1 (SEQ ID NO: 3, 4).

FIG. 3 shows the a) nucleic acid sequence and b) amino acid sequence of SEP protein 2 (SEQ ID NO: 5, 6).

FIG. 4 shows the a) nucleic acid sequence and b) amino acid sequence of SEP protein 3 (SEQ ID NO: 7, 8).

Figure 5:
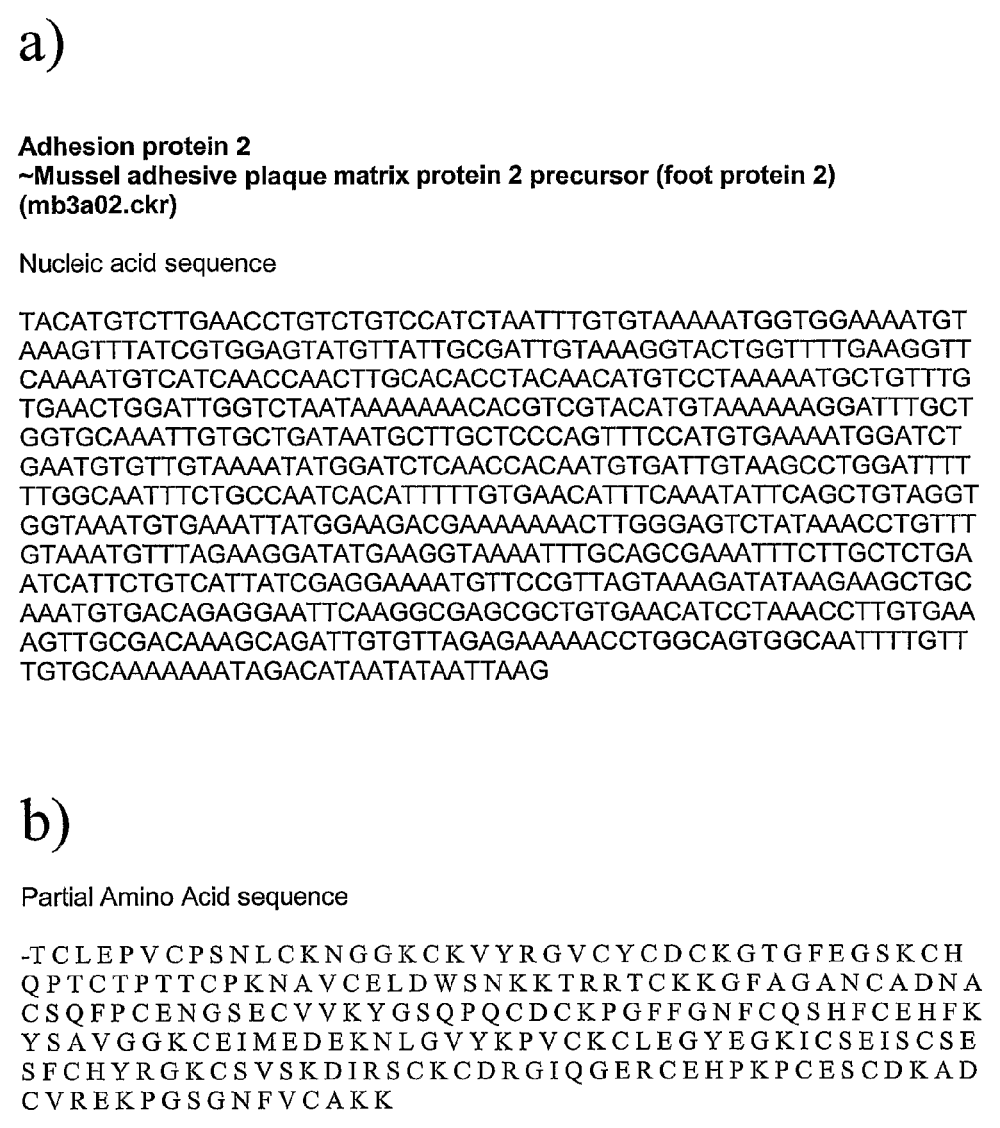

FIG. 5 shows the a) nucleic acid sequence and b) amino acid sequence of adhesion protein 2, homologous to mussel adhesive plaque matrix protein 2 precursor (SEQ ID NO: 9, 10).

FIG. 6 shows the a) nucleic acid sequence and b) amino acid sequence of adhesion protein 1, homologous to mussel adhesive plaque matrix protein precursor (foot protein 1) (SEQ ID NO: 11, 12)

Figure 7:
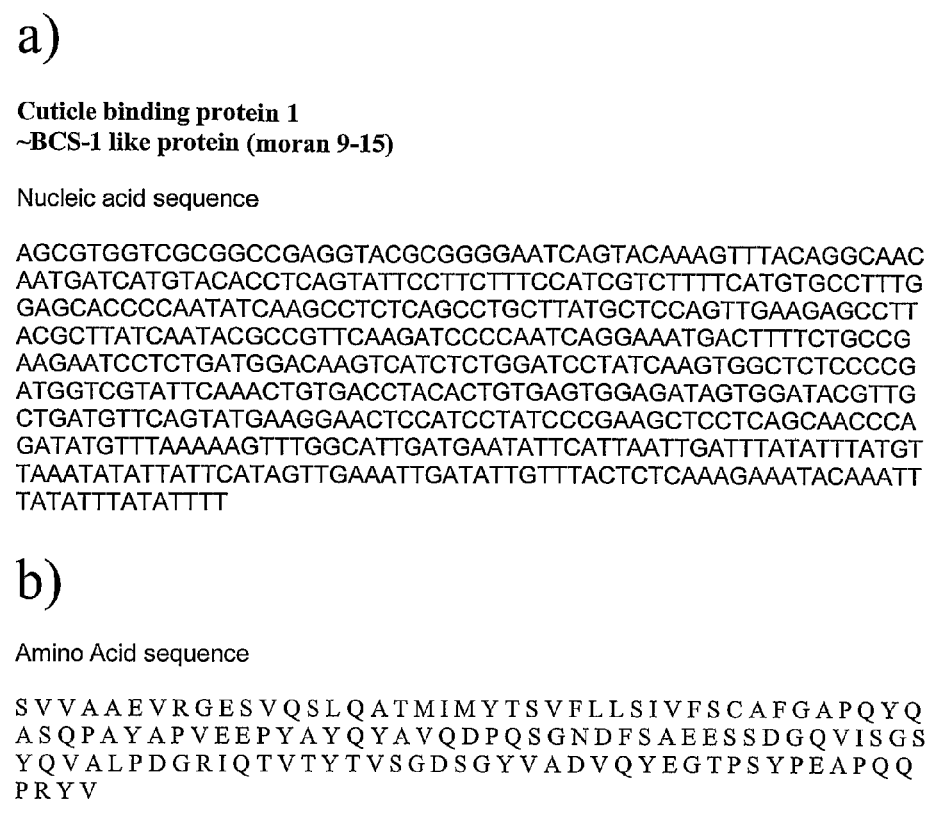

FIG. 7 shows the a) nucleic acid sequence and b) amino acid sequence of cuticle binding protein 1, homologous to BSC-1 like protein (moran 9-15) (SEQ ID NO: 13, 14).

FIG. 11 shows a partial nucleic acid sequence (SEQ ID NO: 15) of vitellogenin-like protein SL-903 similar to but longer than the one in FIG. 1. Bolded, underlined and italicized TGA, TAA or TAG are predicted stop codons.

FIG. 12 shows the full-length nucleic acid sequence of SEP protein 1 SL-0547 (SEQ ID NO: 16). Bolded and underlined ATG are presumed starting codons. Bolded, underlined and italicized TGA, TAA or TAG are predicted stop codons.

FIG. 13 shows the putative full-length nucleic acid sequence of SEP protein 2 SL-0858 (SEQ ID NO: 17). Bolded and underlined ATG are presumed starting codons for protein. Bolded, underlined and italicized TGA, TAA or TAG are predicted stop codons.

FIG. 14 shows the putative full-length sequence of SEP protein 3 SL-1469 (SEQ ID NO: 18). Bolded and underlined ATG are presumed starting codons for protein. Bolded, underlined and italicized TGA, TAA or TAG are predicted stop codons.

FIG. 15 shows the putative full-length sequence of mussel adhesive protein SL-0927 (SEQ ID NO: 19). Bolded and underlined ATG are presumed starting codons for protein. Bolded, underlined and italicized TGA, TAA or TAG are predicted stop codons.

FIG. 16 shows a partial amino acid sequence of vitellogenin-like protein SL-903 (SEQ ID NO: 20), together with BLAST™ hits of the sequence. Underlined amino acids are the peptide fragments from Proteomics Mass Spectrometry data.

FIG. 17 shows the putative full-length amino acid sequence of SEP protein 1 SL-0547 (SEQ ID NO: 21), together with BLAST hits of the sequence. Underlined amino acids are the peptide fragments from Proteomics Mass Spectrometry data.

FIG. 18 shows the putative full-length amino acid sequence of SEP protein 2 SL-0858 (SEQ ID NO: 22), together with BLAST hits of the sequence. Underlined amino acids are the peptide fragments from Proteomics Mass Spectrometry data.

FIG. 19 shows the putative full-length amino acid sequence of SEP protein 3 SL-1469 (SEQ ID NO: 23), together with BLAST hits of the sequence. Underlined amino acids are the peptide fragments from Proteomics Mass Spectrometry data.

FIG. 20 shows the putative full-length amino acid sequence of mussel adhesive protein SL-0927 (SEQ ID NO: 24), together with BLAST hits of the sequence. Underlined amino acids are the peptide fragments from Proteomics Mass Spectrometry data.

DETAILED DESCRIPTION

Figure 8:
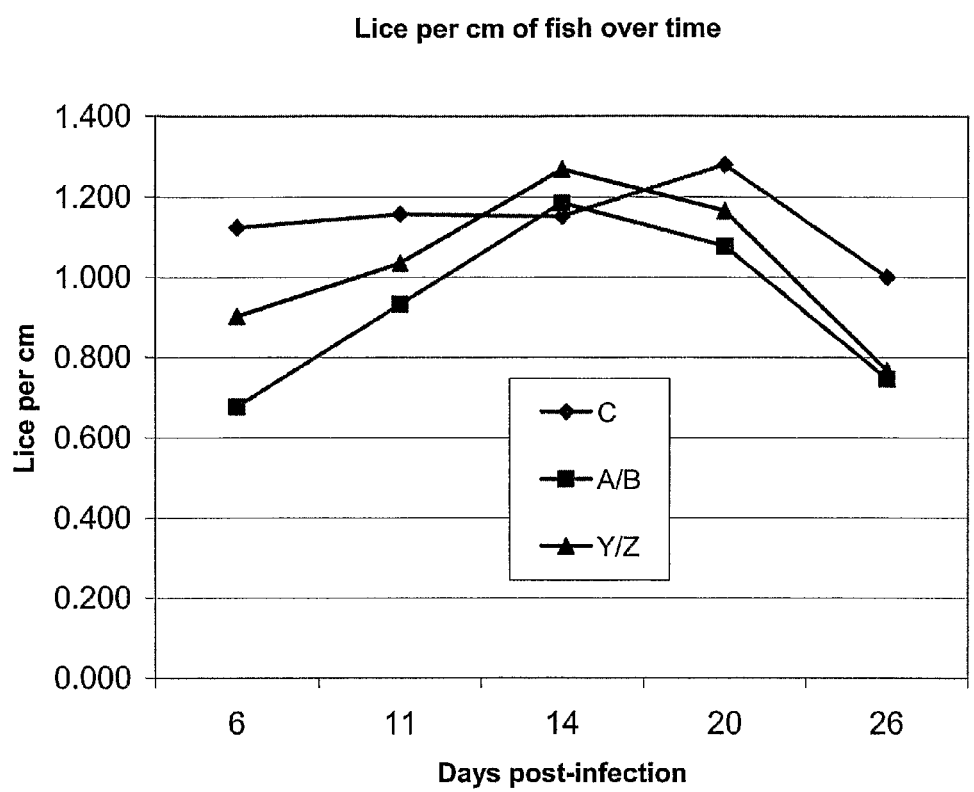
FIG. 8 is a graph of lice per cm of fish over duration of time post-infection, using vaccines (A/B=expressed sea lice trypsin gene with T-cell epitope; Y/Z=expressed sea lice trypsin gene; C=control) of the present invention.

Generally, the present invention provides a vaccine for treating sea lice infection in fish, particularly infection from L. salmonis. It also relates to the DNA and amino acid sequence of molecular targets for use in the preparation of these vaccines.

The vaccines of the present invention were generated based on studies performed by our group and others on gene expression in sea lice. Several genes in sea lice that have the potential as producers of antigens in vaccine formulations designed to protect salmon against sea lice, especially L. salmonis. The genes include: 1) a gene for sea lice trypsin; 2) a gene having high similarity to a vitellogenin-like protein that is found in secretory products; 3) a gene having high sequence similarity to the mussel adhesion protein-1 gene; 4) a gene having high sequence similarity to the mussel adhesion protein-2 gene; 5) a number of genes having high sequence similarity to the gene coding for Balanus amphrite stage specific protein BCS-1; and, 6) genes coding for three secretory products (SP) proteins in sea lice that, at present, have no significant similarity with known proteins in public databases.

As used herein, an "antigen" refers to a molecule containing one or more epitopes that will stimulate a host's immune system to make a humoral and/or cellular antigen-specific response. The term is also used herein interchangeably with "immunogen."

As used herein, the term "epitope" refers to the site on an antigen or hapten to which a specific antibody molecule binds. The term is also used herein interchangeably with "antigenic determinant" or "antigenicdeterminant site."

FIGS. 1 through 6 show the sequences of the genes of the present invention described above and sequenced in our laboratory, with the exception of trypsin, of which the nucleic acid sequence has been published (Johnson, 2002, supra). We have identified trypsin gene product in the sea lice secretions by amino acid sequencing using mass spectrometry. These genes were selected and investigated based on a prior understanding of their putative function.

FIGS. 11 through 20 show longer or putative full-length nucleotide and amino acid sequences of the genes and proteins as described herein.

Antigens derived from *L. salmonis* should provide protection for fish against other sea lice species as they are likely to use highly conserved methods to attach themselves to enable them to successfully feed on the host.

Adjuvants which can be used in the context of the present invention include Montanide™ ISA and IMS Adjuvants (Seppic, Paris, France), other oil-in-water, water-in-oil, and water-in-oil-in-water adjuvants, Ribi's Adjuvants (Ribi ImmunoChem Research, Inc., Hamilton, Mont.), Hunter's TiterMax (CytRx Corp., Norcross, Ga.), aluminum salt adjuvants, nitrocellulose-adsorbed proteins, encapsulated antigens, nanoparticle containing adjuvants. Preferred adjuvants include Seppic Montanide 720, Montanide IMS111x, Montanide IMS131x, Montanide IMS221x, Montanide IMS301x, Montanide ISA206, Montanide ISA 207, Montanide ISA25, Montanide ISA27, Montanide ISA28, Montanide ISA35, Montanide ISA50A, Montanide ISA563, Montanide ISA70, Montanide ISA51, Montanide ISA720, Montanide ISA264. Particularly preferred adjuvants include, Montanide ISA740, Montanide ISA773, Montanide ISA 708, Montanide ISA266. The recommended adjuvant is Montanide ISA763.

Data from studies using the vaccines of the present invention for the treatment of sea lice infection are provided herein by way of the following examples.

Example 1

Figure 9:
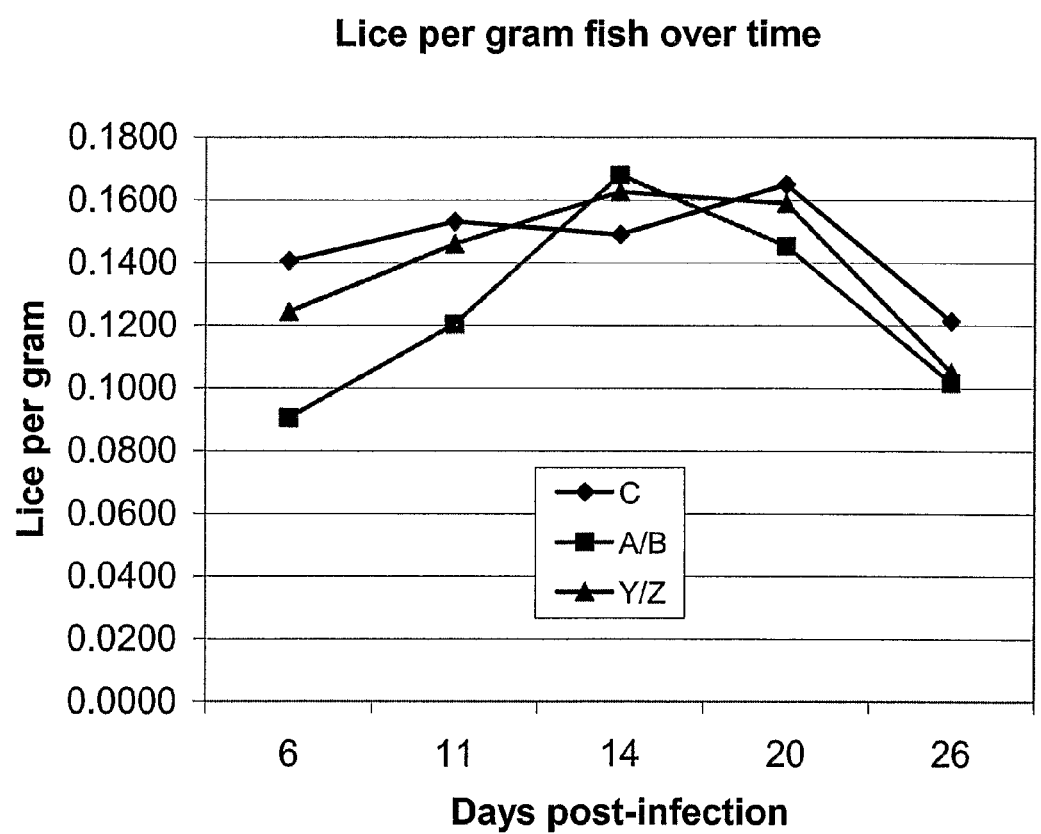
FIG. 9 is a graph of lice per gram of fish over duration of time post-infection, using vaccines (A/B=expressed sea lice trypsin gene with T-cell epitope; Y/Z=expressed sea lice trypsin gene; C=control) of the present invention.

Salmon were challenged with *L. salmonis* trypsin as the antigen. The fish were immunized with two formulation groups of trypsin vaccine: A/B (recombinant sea lice trypsin with a T-cell epitope) and Y/Z (recombinant sea lice trypsin only). Certain fish were administered with a control vaccine, C, containing adjuvant only. Protection of the fish is apparent at days 6, 11 and 20 (FIGS. 8 and 9). The number of sea lice per cm and per gram of fish is reduced in the vaccinated fish as compared to controls. The A/B vaccine formulation resulted in lower lice numbers than the Y/Z formulation showing that the inclusion of T-cell epitopes with sea lice antigens provide further protection against sea lice.

Figure 10:
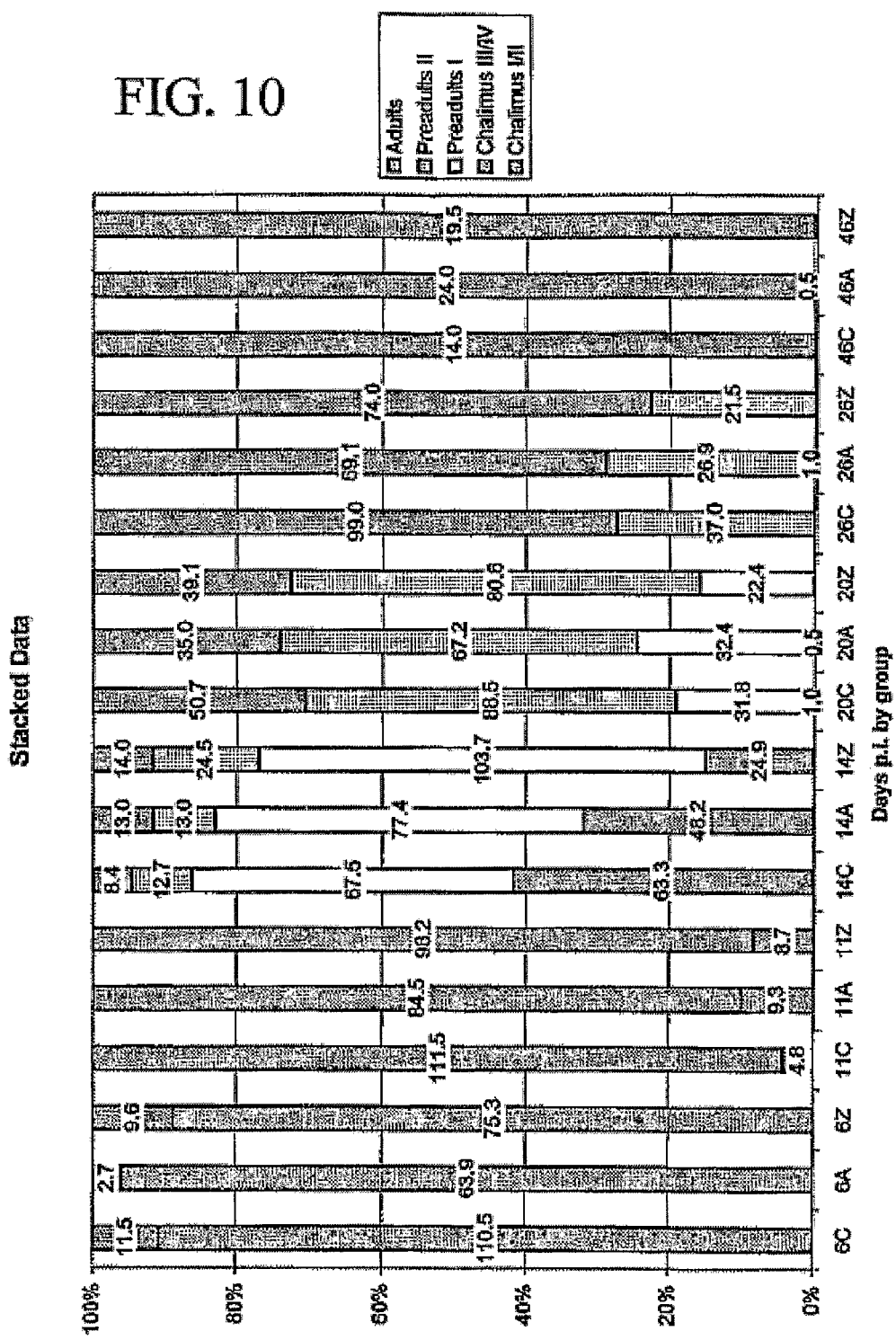
FIG. 10 shows a stacked data graph showing the percentages of different stages of sea lice present in fish immunized with L. salmonis trypsin vaccine as compared to control fish at each sampling time.

FIG. 10 shows stacked data results of the challenge and vaccination experiments. The A/B (recombinant sea lice trypsin with a T-cell epitope) vaccine formulation appeared to slow the development of *L. salmonis*, as at days 6, 11 and 20, there were lower percentages of lice that had moulted to a more advanced stage compared to control fish Example 2

Size Exclusion Chromatography and Protein Determination

Lyophilized secretory excretory products (SEPs) were reconstituted with 1.0 M ammonium acetate (AMA) (pH 6.0). An Agilent 1100 HPLC equipped with a diode array detector (monitoring at 230 and 256 nm) and a Taso Haas (G3000PWX2, 6 μm $d_p$ (7.8 mm×300 mm)) column were used to separate proteins/peptides in the secretions. These samples were then fractionated using a Waters Fraction collector according to time intervals. The fractions as shown in Table 1 were collected for 6 separate HPLC runs and pooled for each time interval. These samples were then freeze dried (−80° C.) prior to protein determination. The column was kept at room temperature and eluted isocratically with 98:2 AMA: acetonitrile (ACN) for 30 minutes at 0.2 ml min$^{-1}$. Standard solutions of bovine serum albumin (BSA) (20 μg, 2.0 μg, and 0.2 μg), SW+DA, and bovine trypsin (40 μg) were all run as controls for peak comparison with SEPs.

Protein concentrations of *L. salmonis* secretory fractions were determined using a dye binding method (Bradford, M. Anal Biochem 72: 248-254, 1976). All assays were run on a Thermomax™ Microplate Reader (Molecular Devices). Samples were reconstituted in ddH$_2$O and then, following protein determination, were split equally between cell-based functional assays and proteomic analysis.

SHK Cell Culture

SHK-1 cells were cultured at 18° C. in 75 cm$^2$ tissue-culture-treated flasks (Costar), in L-15 medium (with 300 mg/L L-glutamine) supplemented with 500 μl gentamicin sulphate (50 mg/mL distilled in water), 365 μl 2-mercaptoethanol (55 mM in D-PBS) and 5% fetal bovine serum (FBS), as described by Fast et al. 2004 supra. All media components were purchased from Gibco. Confluent flasks were passaged weekly by dividing cells and medium evenly between two flasks and adding an equal volume of new media to each flask. Cells used in this study were passaged between 64 and 68 times.

SHK-1 cells were seeded at approximately 4×10$^6$ cells/flask in L-15 medium supplemented as described above. Cell stimulation followed the same procedure as in Fast, M. D. et al. Dev. Comp. Immunol. 29: 951-963, 2005. Briefly, following a 48 h period, to allow any manipulation-induced gene expression to return to constitutive levels, media was removed and 20 ml fresh media was added. Lipopolysaccharide (LPS) was added to all flasks, except the controls, to obtain a final concentration of 5 μg/mL.

In the first trial, SEP fractions were pooled into 3 groups (Table 1), each containing equal time ranges (10 min) and volumes from the size exclusion chromatography. This resulted in 13 μg protein (pooled fraction 1), 8.0 μg protein (pooled fraction 2) and <0.1 μg protein (pooled fraction 3) being added to each flask. These incubations were carried out for 4 h at 18° C. before media was removed and cells stored in RNA later at −80° C. until RNA extraction. This trial was repeated twice with triplicate flasks for each condition.

In the second trial, SEP fractions 1 and 2 from pooled fraction 1 (Table 1) were added at 1.0 and 1.4 μg per flask, respectively. These concentrations were attained after concentrating 4 size exclusion runs for each fraction. To test any affect of residual solvent on the cell-based assay, 4 blank runs of AMA underwent the same treatment and were included in the experiment as controls. Finally, the non-fractionated SEPs used in the macrophage incubations were incubated here at the same concentration (660 ηg). These incubations were carried out in triplicate and followed the same procedure as the first trial.

Real-Time PCR on Atlantic Salmon Genes

Total RNA was isolated from SHK-1 cells stored in RNAlater™ with the Nucleospin™ RNA II kit (Clontech) and concentration measured by spectrophotometer. RNA samples underwent PCR to verify the lack of DNA contamination. Sequences for Real-time PCR primers were designed, tested and products sequenced as previously described by Fast et al., supra (2004; 2005). Real-time quantitative PCR was performed using an iCycler iQ™ Real-Time detection system and SYBR green kits (Bio-Rad) also previously described by Fast et al., supra (2004; 2005). To ensure no genomic DNA contamination added to the quantified cDNA, non-RT controls for each RNA isolation were run under PCR and observed by 2.5% agarose gel electrophoresis.

The PCR profile was as follows: an initial 3 min denaturation step at 95° C., followed by 40 cycles of denaturation (30 s at 95° C.), annealing (30 s at 58° C.) and extension (30 s at 72° C.), and finishing with a final extension step of 72° C. for 5 min. The sensitivity of reactions and amplification of contaminant products such as primer dimers, indiscriminately detected by SYBR green (ie. SYBR green binds to all double stranded DNA), were evaluated by amplifying 10 fold dilutions of the clones ($10^{-2}$ to $10^{-8}$ ng) and duplicate samples as well as by performing a blank without cDNA with each run. The relationship between the threshold cycle (Ct) and the log (RNA) was linear (−3.5<slope<−3.2) for all reactions. Copy numbers were estimated based on the molecular weight of clones and OD 260.

Immunomodulatory Activity of SEP Proteins

Figure 21:
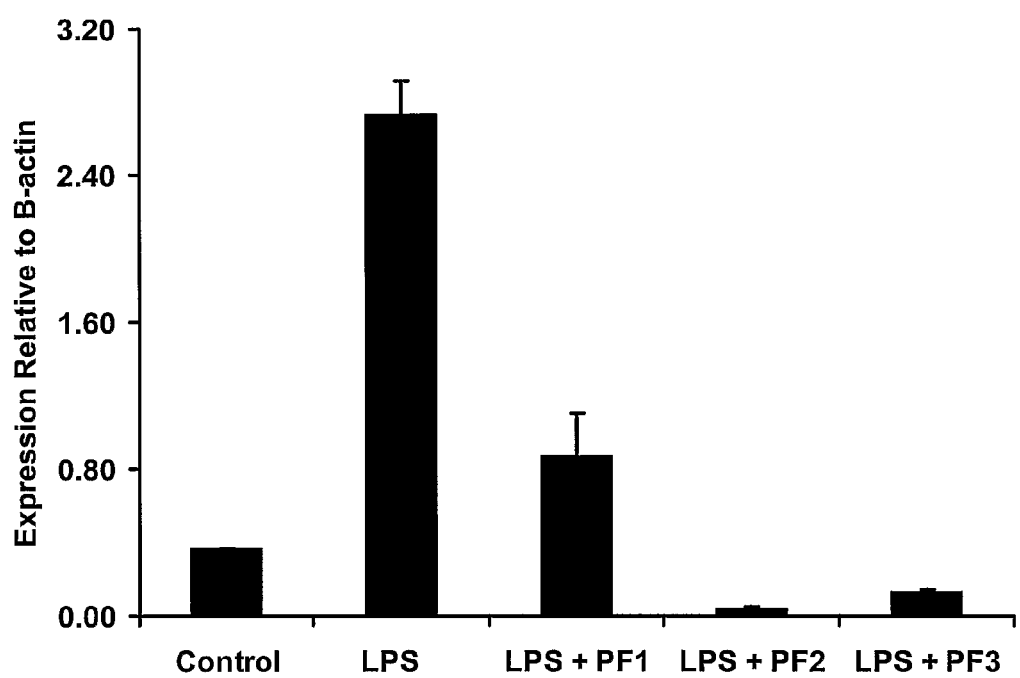
FIG. 21 shows mean (±SEM) expression of interleukin-1β, gene, relative to β-actin, in SHK-1 cells incubated with and without lipopolysaccharide (LPS), pooled L. salmonis secretory/excretory product fraction 1, pooled L. salmonis secretory/excretory product fraction 2, and pooled L. salmonis secretory/excretory product fraction 3. * indicates significant differences from control; † indicates significant differences from LPS+control.
Figure 22:
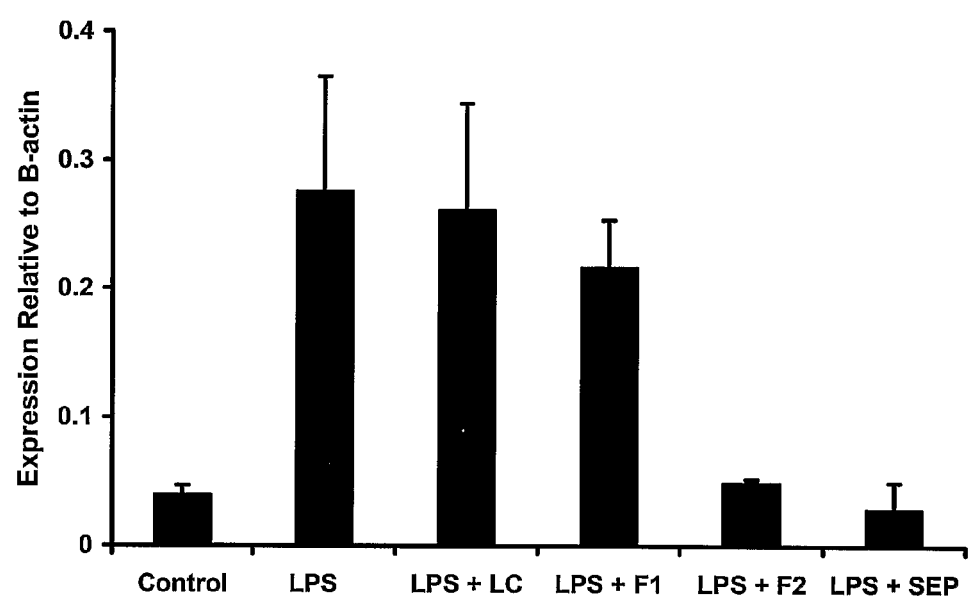
FIG. 22 shows mean (±SEM) expression of interleukin-1β gene, relative to β-actin, in SHK-1 cells incubated with and without lipopolysaccharide (LPS), LPS and lyophilized liquid chromatography solvent (LC), L. salmonis secretory/excretory product fraction 1, L. salmonis secretory/excretory product fraction 2, and L. salmonis unfractionated secretory/excretory products. * indicates significant differences from control; † indicates significant differences from LPS+control.

The SEPs were fractionated based on size and fractions were collected. In the first trial (FIG. 21), pooled fractions (PF1, PF2, PF3) were incubated with SHK-1 cells (a salmon macrophage-like cell line) in combination with lipopolysaccharide (LPS) and the expression of the interleukin-1β gene was monitored in order to determine the immunomodulatory effect of the fractionated SEP proteins on immune gene expression. Interleukin-1β gene was reduced in expression by all three pooled fractions in comparison to cells stimulated with LPS alone (FIG. 21). When individual fractions containing proteins were tested, interleukin-1β gene expression was reduced by fraction 2. LC-MS analysis showed that Fraction 2 of pool 1 contained the SEP protein 1, SEP Protein 2 and trypsin. Evidence for immunomodulatory activity of SEP, which contains all described proteins, is presented in FIG. 22 where there is a significant decrease in LPS-induced expression of interleukin-1β in the presence of total SEPs.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. An immunogenic formulation for reducing caligid copepod infestation in fish, the formulation comprising an immunogenically effective amount of an isolated recombinant antigen comprising a sequence selected from the group consisting of vitellogenin-like protein (SEQ ID NO: 2), SEP protein 1 (SEQ ID NOs:4 and 21), SEP protein 2 (SEQ ID NOs:6 and 22), SEP protein 3 (SEQ ID NOs: 8 and 23), and combinations thereof; and a pharmaceutically-acceptable adjuvant, diluent or carrier.

2. The immunogenic formulation of claim 1 wherein the caligid copepod is *Lepeophtheirus salmonis*.

3. An isolated recombinant antigen consisting of an amino acid sequence selected from the group consisting of vitellogenin-like protein (SEQ ID NO: 2), SEP protein 1 (SEQ ID NOs:4 and 21), SEP protein 2 (SEQ ID NOs:6 and 22), SEP protein 3 (SEQ ID NOs: 8 and 23), and combinations thereof.

4. The formulation according to claim 1, wherein the formulation comprises a pharmaceutically-acceptable adjuvant.

5. The formulation according to claim 4, wherein the pharmaceutically-acceptable adjuvant is selected from the group consisting of: oil-in-water adjuvants, water-in-oil adjuvants, water-in-oil-in-water adjuvants, aluminum salt adjuvants, nitrocellulose-absorbed proteins, encapsulated antigens, and nanoparticle containing adjuvants.

6. The formulation according to claim 1, wherein the formulation comprises a diluent.

7. The formulation according to claim 1, wherein the formulation comprises a carrier.

8. An immunogenic formulation for reducing caligid copepod infestation in fish, the formulation comprising an immunogenically effective amount of an isolated recombinant antigen comprising a sequence which is vitellogenin-like protein (SEQ ID NO: 2); optionally at least one additional protein; and a pharmaceutically-acceptable adjuvant, diluent or carrier.

9. The immunogenic formulation according to claim 8, wherein the at least one additional protein is present and is selected from the group consisting of *L. salmonis* trypsin (SEQ ID NO:25), *L. salmonis* trypsin (SEQ ID NO:26), *L. salmonis* trypsin (SEQ ID NO:27), SEP protein 1 (SEQ ID NOs:4 and 21), SEP protein 2 (SEQ ID NOs:6 and 22), and SEP protein 3 (SEQ ID NOs:8 and 23).

* * * * *